United States Patent
Takahashi et al.

(10) Patent No.: US 8,449,794 B2
(45) Date of Patent: May 28, 2013

(54) NON-RESONANT TWO-PHOTON ABSORPTION RECORDING MATERIAL AND NON-RESONANT TWO-PHOTON ABSORPTION COMPOUND

(75) Inventors: Eri Takahashi, Kanagawa (JP); Masaharu Akiba, Kanagawa (JP); Hiroaki Tsuyama, Kanagawa (JP); Hidehiro Mochizuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/579,578

(22) PCT Filed: Feb. 18, 2011

(86) PCT No.: PCT/JP2011/054212
§ 371 (c)(1),
(2), (4) Date: Aug. 17, 2012

(87) PCT Pub. No.: WO2011/102545
PCT Pub. Date: Aug. 25, 2011

(65) Prior Publication Data
US 2012/0319059 A1    Dec. 20, 2012

(30) Foreign Application Priority Data

Feb. 18, 2010 (JP) .................. 2010-033910
Sep. 29, 2010 (JP) .................. 2010-220085

(51) Int. Cl.
| | |
|---|---|
| *F21V 9/00* | (2006.01) |
| *G02B 5/02* | (2006.01) |
| *G02C 7/10* | (2006.01) |
| *G02F 1/361* | (2006.01) |
| *G03B 11/00* | (2006.01) |
| *C07C 255/00* | (2006.01) |
| *C07C 49/00* | (2006.01) |

(52) U.S. Cl.
USPC ......... 252/582; 428/64.4; 428/64.8; 430/139; 430/270.1; 558/415; 568/332

(58) Field of Classification Search
USPC .............. 252/582; 428/64.4, 64.8; 430/139, 430/270.1; 558/415; 568/332
See application file for complete search history.

(56) References Cited

U.S. PATENT DOCUMENTS

| | | | |
|---|---|---|---|
| 2004/0245432 A1 | 12/2004 | Takizawa | |
| 2009/0246443 A1* | 10/2009 | Akiba et al. | ............ 428/64.8 |
| 2009/0303855 A1 | 12/2009 | Akiba et al. | |
| 2010/0078607 A1* | 4/2010 | Akiba et al. | ............ 252/582 |

FOREIGN PATENT DOCUMENTS

| | | |
|---|---|---|
| JP | 2005-029725 A | 2/2005 |
| JP | 2005-097538 A | 4/2005 |
| JP | 2005-320502 A | 11/2005 |
| JP | 2007-017885 A | 1/2007 |
| JP | 2007-087532 A | 4/2007 |
| JP | 2007-262155 A | 10/2007 |
| JP | 2009-099253 A | 5/2009 |
| JP | 2009-259383 A | 11/2009 |
| JP | 2010-108588 A | 5/2010 |
| WO | 2007/125937 A1 | 11/2007 |

OTHER PUBLICATIONS

International Search Report for PCT/JP2011/054212 dated Mar. 22, 2011 [PCT/ISA/210].
Written Opinion for PCT/JP2011/054212 dated Mar. 22, 2011 [PCT/ISA/237].

* cited by examiner

*Primary Examiner* — Bijan Ahvazi
(74) *Attorney, Agent, or Firm* — Sughrue Mion, PLLC

(57) ABSTRACT

A non-resonant two-photon absorption recording material containing at least (a) a non-resonant two-photon absorption compound, and (b) a recording component in which at least either a refractive index or fluorescence intensity changes, wherein the non-resonant two-photon absorption compound (a) is a compound having a structure represented by formula (1) as described.

14 Claims, No Drawings

NON-RESONANT TWO-PHOTON ABSORPTION RECORDING MATERIAL AND NON-RESONANT TWO-PHOTON ABSORPTION COMPOUND

TECHNICAL FIELD

The present invention relates to a non-resonant two-photon absorption recording material and a non-resonant two-photon absorption compound. More specifically, the invention provides a recording material capable of three dimensionally recording pits in a recording medium and reading the recorded pits by using non-resonant two-photon absorption, which material is capable of non-resonant two-photon absorption recording using a recording light in a wavelength region shorter than 700 nm, and the invention also provides a two-photon absorption compound. The invention further provides a non-resonant two-photon absorption recording material capable of obtaining highly sensitivity by using the two-photon absorption compound having high solubility.

BACKGROUND ART

In general, nonlinear optical effect means a nonlinear optical response proportional to the square, cube or higher power of the applied photoelectric field. As the second order nonlinear optical effects proportional to the square of the applied photoelectric field, second harmonic generation (SHG), optical rectification, photo-refractive effect, Pockels effect, parametric amplification, parametric oscillation, light sum frequency mixing, and light difference frequency mixing are known. As the third order nonlinear optical effects proportional to the cube of the applied photoelectric field, third harmonic generation (THG), optical Kerr effect, self-induced refractive index change and two-photon absorption are exemplified.

As the nonlinear optical materials exhibiting these nonlinear optical effects, a variety of inorganic materials have been found until now. However, it has been very difficult to use inorganic materials in practice for the reason that what is called molecular design to optimize desired nonlinear optical properties or various physical properties necessary to manufacture a device is difficult. On the other hand, organic compounds are not only capable of optimization of desired nonlinear optical properties by molecular design but also capable of control of other various physical properties and the possibility of practical use is high, so that organic materials are attracting public attention as promising nonlinear optical materials.

In recent years, of the nonlinear optical properties of organic compounds, third order nonlinear optical effect, in particular, non-resonant two-photon absorption is becoming the object of public attention. Two-photon absorption is a phenomenon such that a compound is excited by the absorption of two photons simultaneously. The case where two-photon absorption occurs in an energy region where (linear) absorption band of a compound is not present is called non-resonant two-photon absorption. In the following description, "two-photon absorption" means "non-resonant two-photon absorption" even when not especially indicated. Further, "simultaneous two-photon absorption" is sometimes referred to as merely "two-photon absorption" by omitting "simultaneous".

The efficiency of non-resonant two-photon absorption is proportional to the square of photoelectric field applied (quadratic dependency of two-photon absorption). Accordingly, when a laser is irradiated on a two-dimensional plane, two-photon absorption occurs only at the position of high electric field intensity of the center part of laser spot, and two-photon absorption does not occur at all at the peripheral part of weak electric field intensity. On the other hand, in a three-dimensional space, two-photon absorption occurs only in a region having large electric field intensity at the focus where laser rays are converged through a lens, and two-photon absorption does not take place at all in a region being off the focus for the reason that the electric field intensity is weak. As compared with the linear absorption wherein excitation occurs at all the positions in proportion to the intensity of photoelectric field applied, spatial resolution is extraordinarily improved in the non-resonant two-photon absorption, since excitation takes place at only one point in the space due to the quadratic dependency.

In general, in the case of inducing non-resonant two-photon absorption, a short pulsed laser in a near infrared region having no absorption which is on the side longer than the wavelength region where the (linear) absorption band of a compound is present is used in many cases. Since a near infrared ray in what is called a transparent region is used in non-resonant two-photon absorption, an excited light can reach the inside of a sample without being absorbed or scattered, and one point inside the sample can be excited with extremely high spatial resolution due to quadratic dependency of non-resonant two-photon absorption.

Until now, the present applicant has applied for various patents concerning two-photon-sensitizing type three-dimensional recording materials using a compound inducing non-resonant two-photon absorption. These recording materials are recording materials containing at least (1) a two-photon absorption compound (a two-photon sensitizer), and (2) a refractive index modulating material or a fluorescence intensity modulating material, wherein compound (1) efficiently performs two-photon absorption and the acquired photo-energy is delivered to material (2) by means of photo-inductive electron transfer or energy transfer, and recording is conducted by modulating the refractive index or fluorescence intensity of material (2). By using non-resonant two-photon absorption in the light absorption process not one-photon absorption used in ordinary photo-recording, it becomes possible to write recording pits on ordinary position in the inside of the recording material with three-dimensional spatial resolution.

For example, JP-A-2007-87532 (the term "JP-A" as used herein refers to an "unexamined published Japanese patent application") discloses a technique using, as refractive index modulating material or fluorescence intensity modulating material (2), a material capable of modulating a refractive index by color development of a dye, or a material capable of modulating fluorescence by changing from non-fluorescence to fluorescent emission or from fluorescent emission to non-fluorescence (a material capable of modulating a refractive index or fluorescence by color development of a dye or a fluorescent dye). Further, JP-A-2005-320502 discloses a technique using, as refractive index modulating material or fluorescence intensity modulating material (2), a material capable of amplification of recording by forming a seed (a latent image nucleus) of extremely slightly color development of a dye or fluorescence changed, and then light-irradiating or heating (refractive index/fluorescence modulation, a latent image amplification system, a material forming a latent image capable of refractive index/fluorescence modulation by color development of a dye). JP-A-2005-29725 discloses a technique of using, as refractive index modulating material (2), a material capable of modulating a refractive index by forming a polymer by polymerization (a material capable of refractive index modulation by polymerization). Furthermore, JP-A-2005-97538 discloses a technique using, as the refractive index modulating material, a material of forming an extremely minute polymerization latent image nucleus and then actuating polymerization (refractive index modulation, a latent image polymerization system, a material forming a latent image capable of refractive index modulation by polymerization).

Two-photon sensitizing type three-dimensional recording materials in all of JP-A-2007-87532, JP-A-2005-320502, JP-A-2005-29725, JP-A-2005-97538 use, as the two-photon absorption compounds (two-photon sensitizers) (1), compounds actuating two-photon absorption with a light of 700 nm or more. However, in recent years, further various demands have been made. Above all, for obtaining higher recording density, a technique capable of non-resonant two-photon absorption recording by using a recording light in a wavelength region shorter than 700 nm has been required to form smaller pits in a recording material.

For satisfying such a demand, JP-A-2010-108588 discloses a two-photon absorption recording material capable of non-resonant two-photon absorption recording with a recording light in a wavelength region shorter than 700 nm and having sufficient recording and readout properties. JP-A-2010-108588 further discloses a polyphenyl compound having high two-photon absorption ability in the short wavelength region which is usable therein.

SUMMARY OF INVENTION

However, the two-photon absorption recording material disclosed in JP-A-2010-108588 does not also have sufficiently satisfactory sensitivity.

An object of the invention is to overcome insufficient points of the prior art and provide a two-photon absorption recording material capable of non-resonant two-photon absorption recording in high sensitivity with a recording light in a wavelength region shorter than 700 nm and having sufficient recording and readout properties and a two-photon absorption compound usable in the material. Another object is to provide a highly sensitive two-photon absorption recording material using the two-photon absorption compound having high solubility.

As a result of earnest examinations, the present inventors have found that the above problems can be solved by the following constitution.

<1> A non-resonant two-photon absorption recording material comprising:
  (a) a non-resonant two-photon absorption compound, and
  (b) a recording component in which at least either refractive index or fluorescence intensity changes,
wherein the non-resonant two-photon absorption compound (a) is a compound having the structure represented by the following formula (1):

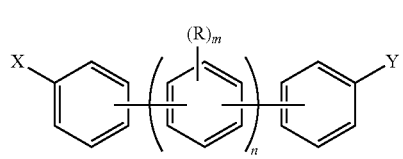

Formula (1)

wherein each of X and Y represents a substituent having a Hammett's sigma para-value (σp value) of 0 or more, which may be the same with or different from each other; n represents an integer of 1 to 4; R represents a substituent, and a plurality of R's may be the same with or different from every other R; and m represents an integer of 0 to 4, provided that when n is 1, m is 1 or more, and when n is 2 or more, at least any of n-groups of phenylene groups is m≧1.

<2> The non-resonant two-photon absorption recording material according to the above <1>, wherein the non-resonant two-photon absorption compound having the structure represented by formula (1) is a compound having the structure represented by the following formula (2):

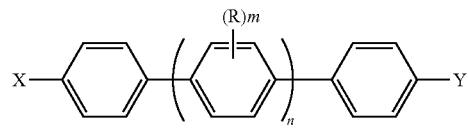

Formula (2)

wherein each of X and Y represents a substituent having a Hammett's sigma para-value (σp value) of 0 or more, which may be the same with or different from each other; n represents an integer of 1 to 4; R represents a substituent, and a plurality of R's may be the same with or different from every other R; and m represents an integer of 0 to 4, provided that when n is 1, m is 1 or more, and when n is 2 or more, at least any of n-groups of phenylene groups is m≧1.

<3> The non-resonant two-photon absorption recording material according to the above <1> or <2>, wherein the non-resonant two-photon absorption compound having the structure represented by formula (1) or (2) is a compound having the structure represented by the following formula (3):

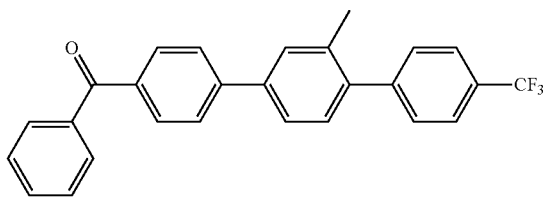

Formula (3)

<4> The non-resonant two-photon absorption recording material according to the above <1> or <2>, wherein the non-resonant two-photon absorption compound having the structure represented by formula (1) or (2) is a compound having the structure represented by the following formula (4):

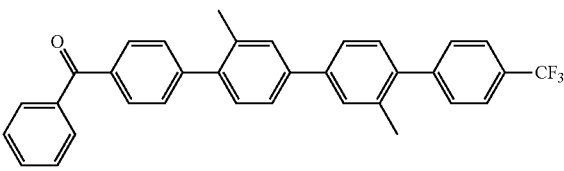

Formula (4)

<5> The non-resonant two-photon absorption recording material according to the above <1> or <2>, wherein the non-resonant two-photon absorption compound having the structure represented by formula (1) or (2) is a compound having the structure represented by the following formula (5):

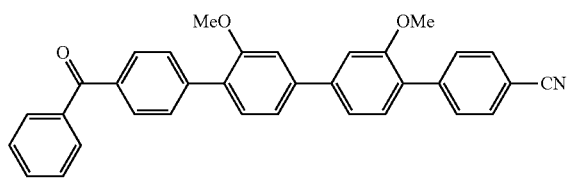

Formula (5)

<6> A non-resonant two-photon absorption recording material comprising:
(a) a non-resonant two-photon absorption compound, and
(b') a polymer binder,
wherein the non-resonant two-photon absorption compound (a) is a compound having the structure represented by the following formula (1):

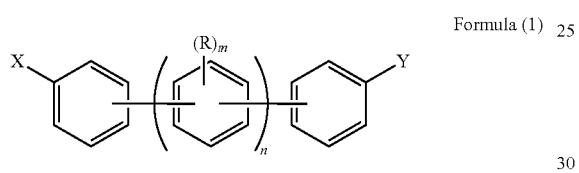

Formula (1)

wherein each of X and Y represents a substituent having a Hammett's sigma para-value (σp value) of 0 or more, which may be the same with or different from each other; n represents an integer of 1 to 4; R represents a substituent, and a plurality of R's may be the same with or different from every other R; and m represents an integer of 0 to 4, provided that when n is 1, m is 1 or more, and when n is 2 or more, at least any of n-groups of phenylene groups is m≧1.

<7> The non-resonant two-photon absorption recording material according to the above <6>, wherein the non-resonant two-photon absorption compound having the structure represented by formula (1) is a compound having the structure represented by the following formula (2):

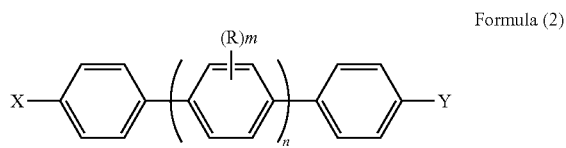

Formula (2)

wherein each of X and Y represents a substituent having a Hammett's sigma para-value (σp value) of 0 or more, which may be the same with or different from each other; n represents an integer of 1 to 4; R represents a substituent, and a plurality of R's may be the same with or different from every other R; and m represents an integer of 0 to 4, provided that when n is 1, m is 1 or more, and when n is 2 or more, at least any of n-groups of phenylene groups is m≧1.

<8> The non-resonant two-photon absorption recording material according to the above <6> or <7>, wherein the non-resonant two-photon absorption compound having the structure represented by formula (1) or (2) is a compound having the structure represented by the following formula (3):

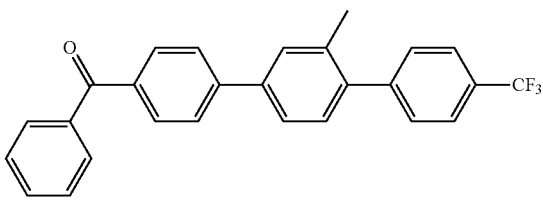

Formula (3)

<9> The non-resonant two-photon absorption recording material according to the above <6> or <7>, wherein the non-resonant two-photon absorption compound having the structure represented by formula (1) or (2) is a compound having the structure represented by the following formula (4):

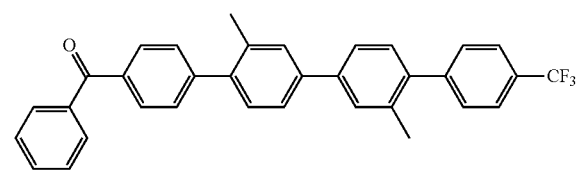

Formula (4)

<10> The non-resonant two-photon absorption recording material according to the above <6> or <7>, wherein the non-resonant two-photon absorption compound having the structure represented by formula (1) or (2) is a compound having the structure represented by the following formula (5):

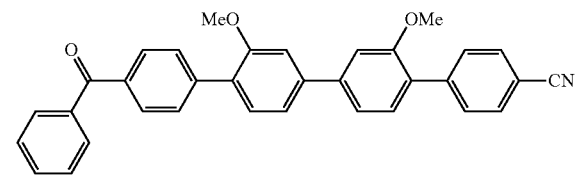

Formula (5)

<11> A compound having the structure represented by the following formula (3):

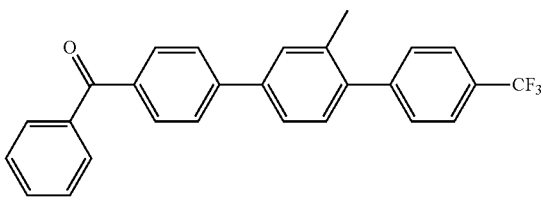

Formula (3)

<12> A compound having the structure represented by the following formula (4):

Formula (4)

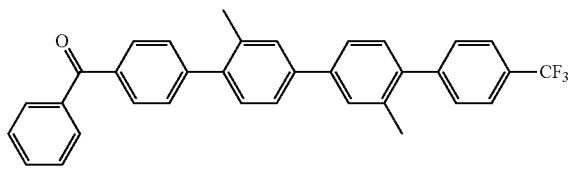

<13> A compound having the structure represented by the following formula (5):

Formula (5)

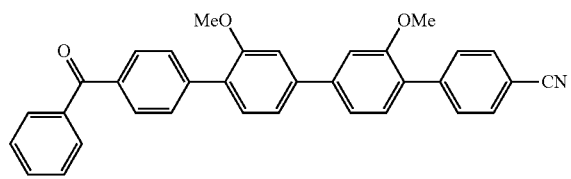

The functional mechanism of the two-photon absorption recording material of the invention being capable of performing non-resonant two-photon absorption recording using a recording light in a wavelength region shorter than 700 nm in high sensitivity is not clearly known, but it is presumed for the reason that the solubility in a solvent of the two-photon absorption compound (the polyphenyl compound represented by formula (1)) used in the two-photon absorption recording material is improved and the compound can be contained in the recording material in high concentration due to the presence of proper substituent R on at least any of phenylene groups of the non-terminal.

According to the constitution of the two-photon absorption recording material of the invention, it is possible to perform non-resonant two-photon absorption recording using a recording light in a wavelength region shorter than 700 nm in high sensitivity and obtain sufficient recording and readout properties.

In addition, the two-photon absorption compound in the invention shows non-resonant two-photon absorption properties by the recording light in a wavelength region shorter than 700 nm and high two-photon absorption cross sectional area can be obtained. Further, the two-photon absorption compound in the invention has high solubility and can be contained in the two-photon absorption recording material in high concentration, and so high recording sensitivity can be obtained by the recording material.

DESCRIPTION OF EMBODIMENTS

The two-photon absorption recording material in the invention will be described in detail below.

Two-photon absorption recording materials described in the specification of the invention include two kinds of forms, i.e., [A] a two-photon absorption recording material containing (a) a non-resonant two-photon absorption compound, and (b) a recording component in which at least either refractive index or fluorescence intensity changes, and [B] two-photon absorption recording material containing (a) a non-resonant two-photon absorption compound, and (b') a polymer binder, and these two kinds of forms are described in order.

[A] Two-photon absorption recording material containing (a) non-resonant two-photon absorption compound, and (b) recording component in which at least either refractive index or fluorescence intensity changes (hereinafter also referred to as "two-photon absorption recording material [A])"

<Non-Resonant Two-Photon Absorption Compound>

The non-resonant two-photon absorption compound (a) for sue in the non-resonant two-photon absorption recording material [A] of the invention will be described below.

The non-resonant two-photon absorption compound (a) for sue in the non-resonant two-photon absorption recording material of the invention is a compound having the structure represented by the following formula (1).

Formula (1)

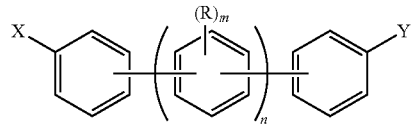

In formula (1), each of X and Y represents a substituent having a Hammett's sigma para-value (σp value) of 0 or more, which may be the same with or different from each other; n represents an integer of 1 to 4; R represents a substituent, and a plurality of R's may be the same with or different from every other R; and m represents an integer of 0 to 4, provided that when n is 1, m is 1 or more, and when n is 2 or more, at least any of n-groups of phenylene groups is m≧1.

In formula (1), each of X and Y indicates a group having a σp value in Hammett's rule of 0 or more, i.e., an electron-withdrawing group. The examples of the electron-withdrawing groups preferably include a trifluoromethyl group, a heterocyclic group, a halogen atom, a cyano group, a nitro group, an alkylsulfonyl group, an arylsulfonyl group, a sulfamoyl group, a carbamoyl group, an acyl group, an acyloxy group, and an alkoxycarbonyl group, more preferably a trifluoromethyl group, a cyano group, an acyl group, an acyloxy group, a bromine atom, and an alkoxycarbonyl group, and most preferably a benzoyl group, a trifluoromethyl group, and a cyano group. Of these substituents, each of a benzoyl group, an alkylsulfonyl group, an arylsulfonyl group, a sulfamoyl group, a carbamoyl group, an acyl group, an acyloxy group and an alkoxycarbonyl group may further have a substituent for various purposes including dissolution in a solvent. As the substituents, an alkyl group, an alkoxy group, an alkoxyalkyl group and an aryloxy group are preferably exemplified.

n represents an integer of 1 to 4, more preferably 2 or 3, and most preferably 2. When n is 5 or more and the more, the more appears the linear absorption on the longer wavelength side, and so non-resonant two-photon absorption recording cannot be done with a recording light in the wavelength region shorter than 700 nm.

R represents a substituent, and the substituent is not especially restricted. Specifically an alkyl group, an alkoxy group, an alkoxyalkyl group and an aryloxy group are exemplified. m represents an integer of 0 to 4, provided that when n is 1, m is 1 or more, and when n is 2 or more, at least any of n-groups of phenylene groups is m≧1.

In the compound having the structure represented by formula (1), the reason that each of X and Y preferably represents a group having a σp value taking a positive value in Hammett's rule, what is called an electron-withdrawing group, is described below.

According to T. Kogej, et al., *Chem. Phys. Lett.*, 298, 1 (1998), two-photon absorption efficiency of an organic compound, i.e., two-photon absorption cross sectional area δ, is in the following relationship with the imaginary number part of tertiary molecule polarizability (second-order hyperpolarizability) γ.

$$\delta(\omega) = \left(\frac{3\pi h v^2}{n^2 c^2 \varepsilon_0}\right) \mathrm{Im}\gamma(-\omega; \omega, -\omega, \omega) \quad \text{Equation (1)}$$

In equation (1), c: light velocity, v: frequency, n: refractive index, $\varepsilon_0$: dielectric constant in vacuum, ω: number of vibration of photon, and Im: imaginary number part. The imaginary number part of γ (Imγ) is in the following relationship with the dipole moment between |g> and |e>: Mge, the dipole moment between |g> and |e'>: Mge', the difference in the dipole moment between |g> and |e>: Δμge, transition energy: Ege, and damping factor: Γ.

$$\mathrm{Im}\gamma(-\omega; \omega, -\omega, \omega) = \quad \text{Equation (2)}$$

$$\mathrm{Im}\, P \sum_{e'} \left[ \begin{array}{c} \dfrac{Mge^2 \Delta\mu ge^2}{(Ege - \hbar\omega - i\Gamma ge)(Ege - 2\hbar\omega - i\Gamma ge)} + \\ (Ege - \hbar\omega - i\Gamma ge) \\ \dfrac{Mge^2 Mee'^2}{(Ege - \hbar\omega - i\Gamma ge)(Ege' - 2\hbar\omega - i\Gamma ge')} - \\ (Ege - \hbar\omega - i\Gamma ge) \\ \dfrac{Mge^4}{(Ege - \hbar\omega - i\Gamma ge)(Ege + \hbar\omega + i\Gamma ge)} \\ (Ege - \hbar\omega - i\Gamma ge) \end{array} \right]$$

In equation (2), P represents a commutative operator.

Accordingly, it is possible to forecast the two-photon absorption cross-sectional area of a compound by computing the value of equation (2). The most stable structure of the ground state is computed by DFT method using B3LYP functional with 6-31 G* as base function, and on the basis of the result, by computing Mge, Mee' and Ege, the value of Imγ can be computed. For example, in a compound having the structure represented by formula (1), when the maximum value of Imγ obtained from the computation of a quaterphenyl compound in which a methoxy group that is an electron-donating substituent is substituted on X and Y is taken as 1, the relative value of the maximum value of Imγ of a molecule having a up value taking a positive value in Hammett's rule, i.e., what is called an electron-withdrawing group as other substituent becomes large.

In a compound having the structure represented by formula (1), as to a quaterphenyl compound in which a methoxy group that is an electron-donating group is substituted on X and Y, Imγ is small, and in a molecule in which each of X and Y is substituted with an electron-withdrawing substituent, Imγ generally greatly increases. As is also described above, since two-photon absorption cross-sectional area δ is theoretically proportional to the imaginary number part of tertiary hyperpolarizability γ, i.e., Imγ, it is preferred from these computations that each of X and Y has a structure substituted with an electron-withdrawing substituent.

The compound having the structure represented by formula (1) is preferably a compound having the structure represented by the following formula (2).

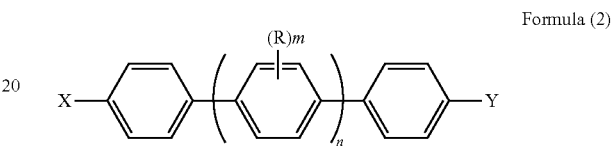

Formula (2)

In formula (2), X, Y, n, R and m are respectively the same with those as defined in formula (1).

In the compound having the structure represented by formula (1) or (2), X and Y may be the same with or different from each other, but they are preferably different for the reason that the two-photon absorption cross-sectional area shows a tendency to be great.

The compound having the structure represented by formula (1) or (2) has substituent R on the phenylene group of the central part of the molecular structure (when two or more phenylene groups are present, at least any of them), and a twist is caused in the molecular structure, as a result symmetry of the compound lowers. Therefore, it is expected that the solubility of the compound having the structure represented by formula (1) or (2) is conspicuously improved as compared with a compound having the same structure and not having substituent R.

The compound having the structure represented by formula (1) or (2) is not especially restricted and, for example, the following are exemplified.

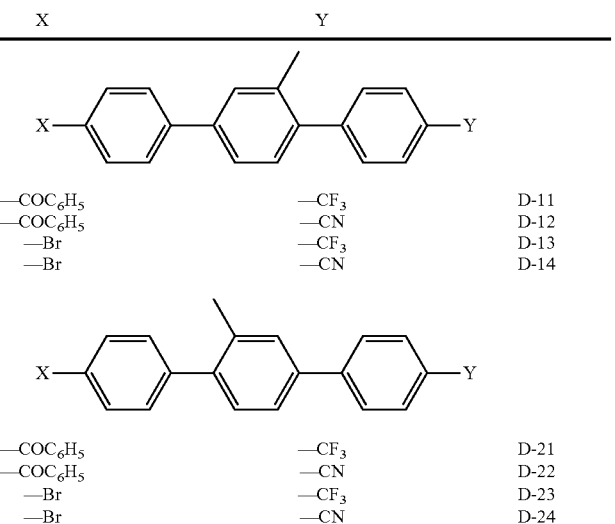

-continued
| X | Y | |
|---|---|---|
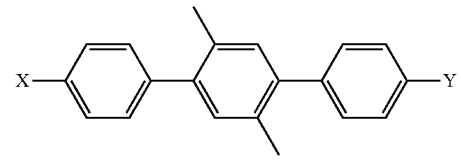
| —COC₆H₅ | —CF₃ | D-31 |
| —COC₆H₅ | —CN | D-32 |
| —Br | —CF₃ | D-33 |
| —Br | —CN | D-34 |
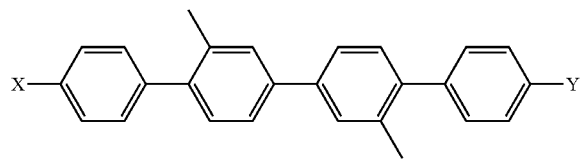
| —COC₆H₅ | —CF₃ | D-41 |
| —COC₆H₅ | —CN | D-42 |
| —Br | —CF₃ | D-43 |
| —Br | —CN | D-44 |
| —CN | —COOC₆H₅ | D-45 |
| —CN | —COOCH₃ | D-46 |
| —CF₃ | —COOC₆H₅ | D-47 |
| —CF₃ | —COOCH₃ | D-48 |
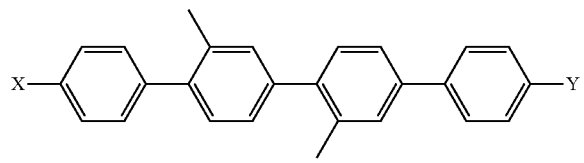
| —COC₆H₅ | —CF₃ | D-51 |
| —COC₆H₅ | —CN | D-52 |
| —Br | —CF₃ | D-53 |
| —Br | —CN | D-54 |
| —CN | —COOC₆H₅ | D-55 |
| —CN | —COOCH₃ | D-56 |
| —CF₃ | —COOC₆H₅ | D-57 |
| —CF₃ | —COOCH₃ | D-58 |
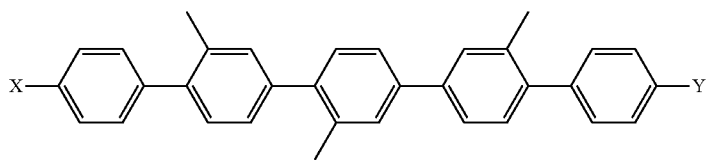
| —COOC₆H₅ | —CF₃ | D-61 |
| —COOC₆H₅ | —CN | D-62 |
| —Br | —CF₃ | D-63 |
| —Br | —CN | D-64 |
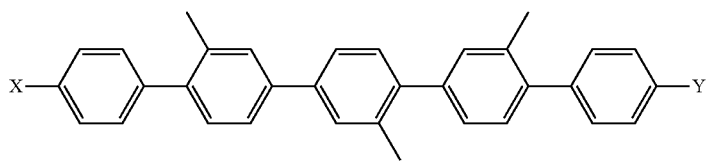
| —COC₆H₅ | —CF₃ | D-71 |
| —COC₆H₅ | —CN | D-72 |
| —Br | —CF₃ | D-73 |
| —Br | —CN | D-74 |

-continued

| X | Y | |
|---|---|---|
| —COC₆H₅ | —CF₃ | D-81 |
| —COC₆H₅ | —CN | D-82 |
| —Br | —CF₃ | D-83 |
| —Br | —CN | D-84 |

| X | Y | |
|---|---|---|
| —COC₆H₅ | —CF₃ | D-91 |
| —COC₆H₅ | —CN | D-92 |
| —Br | —CF₃ | D-93 |
| —Br | —CN | D-94 |

| X | Y | |
|---|---|---|
| —COC₆H₅ | —CF₃ | D-101 |
| —COC₆H₅ | —CN | D-102 |
| —Br | —CF₃ | D-103 |
| —Br | —CN | D-104 |

| X | Y | |
|---|---|---|
| —COC₆H₅ | —CF₃ | D-201 |
| —COC₆H₅ | —CN | D-202 |
| —Br | —CF₃ | D-203 |
| —Br | —CN | D-204 |

D-301
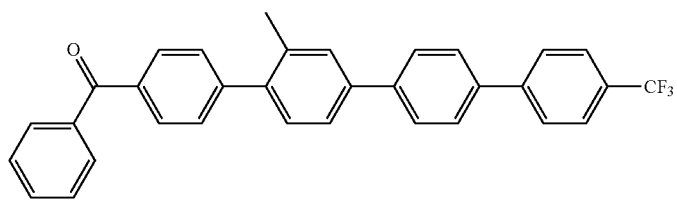
D-302
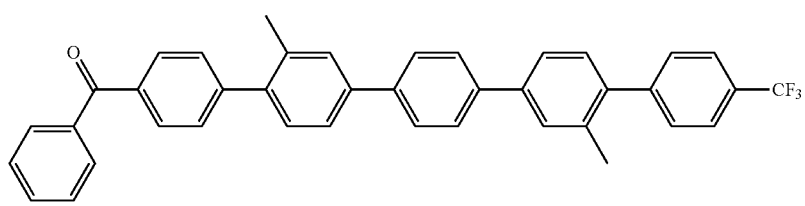
D-303
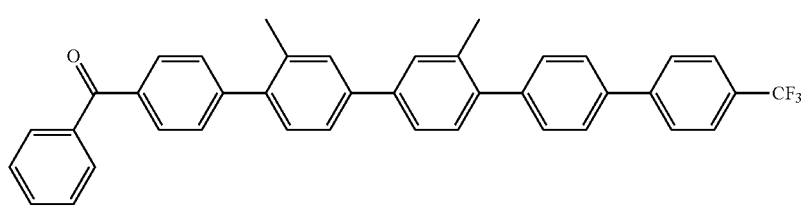
D-304
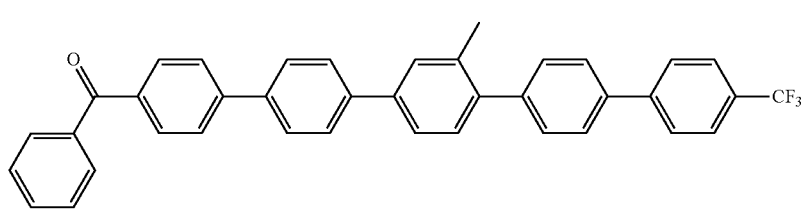
D-401
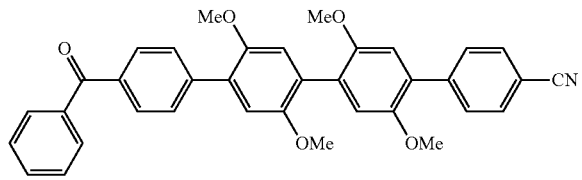
D-402
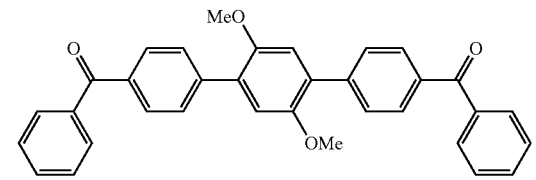
D-403
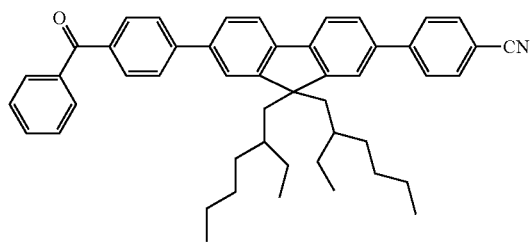
D-404
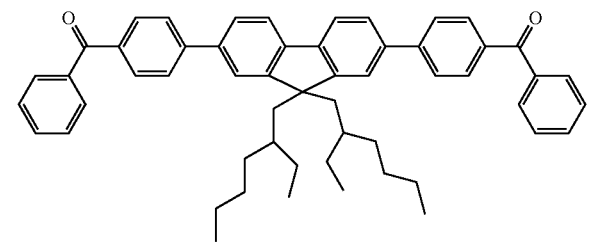
D-405
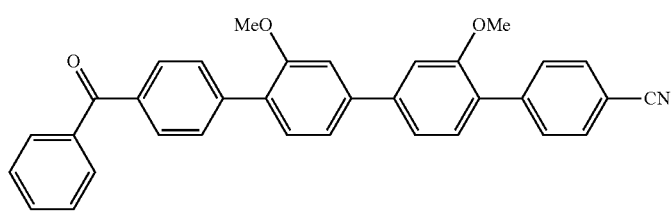

Of the above compounds, D-11 to 13, D-21 to 23, D-41 to 43, and D-405 are preferred compounds, and D-11, D-41, D-401 to D-405 are novel compounds.

<Recording Component in which at Least Either Refractive Index or Fluorescence Intensity Changes>

As (b) recording component in which at least either refractive index or fluorescence intensity changes for use in the non-resonant two-photon absorption recording material of the invention, for example, the following are exemplified. Each component will be explained below in order.

(I) Materials capable of modulating a refractive index or fluorescence by color development of a dye or a fluorescent dye
(II) Materials capable of modulating a refractive index by polymerization
(III) Materials capable of modulating a refractive index by polymerization of a dye having a polymerizable group
(IV) Materials forming a latent image capable of refractive index/fluorescence modulation by color development of a dye
(V) Materials forming a latent image capable of refractive index/fluorescence modulation by polymerization

[Materials Capable of Modulating a Refractive Index or Fluorescence by Color Development of a Dye or a Fluorescent Dye]

As the materials capable of modulating a refractive index or fluorescence by color development of a dye or a fluorescent dye, for example, it is preferred to contain at least one of the following:

(A) A dye precursor in which an absorption band comes out in a visible region by an acid
(B) A dye precursor in which an absorption band comes out in a visible region by a base
(C) A dye precursor in which an absorption band comes out in a visible region by oxidation
(D) A dye precursor in which an absorption band comes out in a visible region by reduction Each of these dye precursors will be described below.

(A) A Dye Precursor in which an Absorption Band Comes Out in a Visible Region by an Acid The dye precursor is a dye precursor capable of becoming a color developer whose absorption property changes from the original state by assistance of an acid generated by an acid generator. As the acid-color development type dye precursor, a compound whose absorption is shifted to longer wavelength side by an acid is preferred, and a compound which develops a color from colorless by an acid is more preferred.

The examples of the acid-color development type dye precursors preferably include triphenylmethane-based, phthalide-based (including indolylphthalide-based, azaphthalide-based, and triphenylmethanephthalide-based), phenothiazine-based, phenoxazine-based, fluoran-based, thiofluoran-based, xanthene-based, diphenyl-methane-based, chromenopyrazole-based, leucoauramine-based, methine-based, azomethine-based, rhodamine lactam-based, quinazoline-based, diazaxanthene-based, fluorene-based, and spiropyran-based compounds. The specific examples of these compounds are disclosed, e.g., in JP-A-2002-156454 and patents cited therein, JP-A-2000-281920, JP-A-11-279328 and JP-A-8-240908.

The acid-color development type dye precursors are more preferably leuco dyes having a partial structure such as lactone, lactam, oxazine, or spiropyran, and fluoran-based, thiofluoran-based, phthalide-based, rhodamine lactam-based, and spiropyran-based compounds are exemplified, and xanthene (fluoran) dyes and triphenylmethane dyes are still more preferred. These acid-color development type dye precursors may be used as mixture of two or more kinds in an arbitrary proportion, if necessary.

The preferred specific examples of the acid-color development type dye precursors are disclosed in JP-A-2007-87532. For example, formulae (21) to (23), the compounds shown in paragraph [0122] (phthalide-based dye precursors (including indolylphthalide-based dye precursors and azaphthalide-based dye precursors)), formula (24), paragraph [0126] (triphenylmethanephthalide-based dye precursors), formula (25), paragraph [0130] (fluoran-based dye precursors), paragraph [0131] (rhodamine lactam-based dye precursors), and paragraph [0132] (spiropyran-based dye precursors) can be used.

As the acid-color development type dye precursors, the BLD compound represented by formula (6) disclosed in JP-A-2000-284475, the leuco dyes disclosed in JP-A-2000-144004, and the leuco dyes having the structures as shown by [Chem. 38] disclosed in JP-A-2007-87532 can also be preferably used.

The compounds represented by formula (26), [Chem. 40], disclosed in JP-A-2007-87532, which develop a color by addition of an acid (proton), can also be used as the acid-color development type dye precursor.

As the preferred specific examples of the acid-color development type dye precursors, the above compounds disclosed in JP-A-2007-87532 are exemplified but the invention is not limited to these compounds.

(B) A Dye Precursor in which an Absorption Band Comes Out in a Visible Region by a Base The dye precursor is a dye precursor capable of becoming a color developer whose absorption property changes from the original state by assistance of a base generated by a base generator.

As the base-color development type dye precursor, a compound whose absorption is shifted to longer wavelength side by a base is preferred, and a compound capable of largely increasing a molar extinction coefficient by a base is more preferred.

The base-color development type dye precursor in the invention is preferably a non-dissociated form of a dissociation type dye. The dissociation type dye is a compound having a dissociative group having a pKa of 12 or less, preferably 10 or less, on the dye chromophore and capable of easily dissociating to release a proton and absorption is shifted to the longer wavelength side or the colorless state turns to the color-developed state by changing from the non-dissociation form to the dissociation form. The preferred examples of the dissociative groups include an OH group, an SH group, a COOH group, a $PO_3H_2$ group, an $SO_3H$ group, an $NR^{91}R^{92}H^+$ group, an $NHSO_2R^{93}$ group, a $CHR^{94}R^{95}$ group, and an $NHR^{96}$ group.

Here, each of $R^{91}$, $R^{92}$ and $R^{96}$ independently represents a hydrogen atom, an alkyl group (preferably having a carbon number of 1 to 20, e.g., methyl, ethyl, n-propyl, isopropyl, n-butyl, n-pentyl, benzyl, 3-sulfopropyl, 4-sulfobutyl, carboxymethyl, 5-carboxypentyl), an alkenyl group (preferably having a carbon (C) number of 2 to 20, e.g., vinyl, allyl, 2-butenyl, 1,3-butadienyl), a cycloalkyl group (preferably having a carbon number of 3 to 20, e.g., cyclopentyl, cyclohexyl), an aryl group (preferably having a carbon number of 6 to 20, e.g., phenyl, 2-chlorophenyl, 4-methoxyphenyl, 3-methylphenyl, 1-naphthyl), or a heterocyclic group (preferably having a carbon number of 1 to 20, e.g., pyridyl, thienyl, furyl, thiazolyl, imidazolyl, pyrazolyl, pyrrolidino, piperidino, morpholino), and preferably a hydrogen atom or an alkyl group. $R^{93}$ represents an alkyl group, an alkenyl group, a cycloalkyl group, an aryl group, or a heterocyclic group (the preferred substituents are the same with the examples of the substituents exemplified in $R^{91}$, $R^{92}$ and $R^{96}$), preferably an alkyl group which may be substituted, or an aryl group which may be substituted, and more preferably an alkyl group which may be substituted, and the substituent at that time is preferably an electron-withdrawing group and is preferably fluorine.

Each of $R^{94}$ and $R^{95}$ independently represents a substituent (the preferred substituents are the same with the examples of the substituents exemplified in $R^{91}$, $R^{92}$ and $R^{96}$). Electron-withdrawing substituents are preferred, and a cyano group, an alkoxycarbonyl group, a carbamoyl group, an acyl group, an alkylsulfonyl group, and an arylsulfonyl group are preferred.

As the dissociative groups of dissociation type dye in the invention, an OH group, an SH group, a COOH group, a $PO_3H_2$ group, an $SO_3H$ group, an $NR^{91}R^{92}H^+$ group, an $NHSO_2R^{93}$ group, and a $CHR^{94}R^{95}$ group are more preferred, an OH group and a $CHR^{94}R^{95}$ group are still more preferred, and an OH group is most preferred.

A preferred non-dissociated form of a dissociation type dye as the base-color development type dye precursor in the invention is preferably a non-dissociated form of a dissociation type azo dye, a dissociation type azomethine dye, a dissociation type oxonol dye, a dissociation type arylidene dye, a dissociation type xanthene (fluoran) dye, or a dissociation type triphenylamine type dye, and a non-dissociated form of a dissociation type azo dye, a dissociation type azomethine dye, a dissociation type oxonol dye, or a dissociation type arylidene dye is more preferred.

As the preferred specific examples of the base-color development type dye precursors, the compounds disclosed in JP-A-2007-87532, paragraphs [0144] to [0146] are exemplified, but the invention is not restricted thereto.

(C) A Dye Precursor in which an Absorption Band Comes Out in a Visible Region by Oxidation The dye precursor is not especially restricted so long as it is a compound capable of increasing the extinction thereof, but it is preferred to contain at least one or more compounds of leucoquinone compounds, thiazineleuco compounds, oxazineleuco compounds, phenazineleuco compounds, and leucotriarylmethane compounds.

As the leucoquinone compounds, compounds having a partial structure represented by any of formulae (6) to (10), paragraphs [0149] to [0150] in JP-A-2007-87532 can be used.

As the thiazineleuco compounds, oxazineleuco compounds and phenazineleuco compounds, the compounds represented by formula (11) or (12), paragraphs [0156] to [0160] in JP-A-2007-87532 can be used.

As the leucotriarylmethane compounds, compounds having a partial structure represented by formula (13), paragraphs [0166] and [0167] in JP-A-2007-87532 are preferably used.

As the preferred specific examples of the dye precursors used in the invention in which an absorption band comes out in a visible region by oxidation, the compounds disclosed in JP-A-2007-87532, paragraph [0152] (leucoquinone compounds), compounds disclosed in the same document, paragraphs [0162] to [0164] (thiazineleuco compounds, oxazineleuco compounds, phenazineleuco compounds), and compounds disclosed in the same document, paragraphs [0169] to [0170] (leucotriarylmethane compounds) are exemplified, but the invention is not restricted thereto.

(D) A Dye Precursor in which an Absorption Band Comes Out in a Visible Region by Reduction As the dye precursor, the compound represented by formula (A) disclosed in JP-A-2007-87532 can be used, and specifically the compounds described in paragraphs [0172] to [0195] of the same document can be used.

When the recording component of the invention includes the dye precursor, it is also preferred for the two-photon absorption recording material of the invention to further contain a base, if necessary, for the purpose of dissociating a dissociation type dye to be generated. The base may be an organic base or inorganic base, and preferably, for example, alkylamines, anilines, imidazoles, pyridines, carbonates, hydroxide salts, carboxylates, and metal alkoxides are exemplified. Alternatively, polymers containing any of these bases are also preferably used.

The above dye precursors for use in the invention can be commercially available, or they can be synthesized according to known methods.

In two-photon recording process, spectral change due to color development of a dye precursor at the site where recording by two-photon absorption recording is carried out preferably appears in the wavelength region longer than the maximum wavelength of linear absorption spectrum of the two-photon absorption dye. Alternatively, it is preferred that the absorption spectral change comes out in the wavelength region shorter than the readout wavelength, and the absorption spectral change is not present at the readout wavelength. By such constitution, it becomes possible to efficiently read out a recording signal by reflected light by making use of large refractive index change coming out on the wavelength side longer than the maximum wavelength of the color developing dye absorption resulting from unusual dispersion of refractive index appearing due to color development of the dye.

In two-photon recording process, spectral change due to achromatization of a dye at the site where recording by two-photon absorption recording is carried out preferably appears in the readout wavelength or the wavelength region shorter than the readout wavelength, and dye absorption is not present at the readout wavelength. By such constitution, refractive index change at the readout wavelength can be increased, so that it becomes possible to efficiently read out a recording signal by reflected light.

As other components in addition to the above, the optical recording material in the invention can contain electron-donating compounds capable of donating electrons to the two-photon absorption compounds or/and the compounds constituting the recording components, acid generators and base generators, according to necessity. As the electron-donating compounds, the compounds disclosed in JP-A-2007-87532, paragraphs [0199] to [0217], as the acid generators, the compounds disclosed in the same document, paragraphs [0218] to [0245], and as the base generators, the compounds in paragraphs [0246] to [0267] can be respectively used.

Materials capable of modulating a refractive index or fluorescence by color development of a dye or a fluorescent dye are disclosed in detail in JP-A-2007-87532.

[Materials Capable of Modulating a Refractive Index by Polymerization]

The material capable of modulating a refractive index by polymerization comprises at least a polymerizable compound and a polymerization initiator. The materials are described in detail below.

(Polymerizable Compound)

The polymerizable compound is a compound capable of oligomerization or polymerization by causing addition polymerization by a radical or acid (a Brønsted acid or a Lewis acid).

The polymerizable compound may be mono-functional or poly-functional, may be one-component or multi-component, may be a monomer, prepolymer (e.g., a dimer, an oligomer), or mixture of them, and the form may be a liquid or solid state.

The polymerizable compound is roughly classified into a polymerizable compound capable of radical polymerization and a polymerizable compound capable of cationic polymerization.

As the radically polymerizable compound, a compound having at least one ethylenically unsaturated double bond in the molecule is preferred, and specifically the following polymerizable monomers, and prepolymers (a dimer, an oligomer, and the like) comprising these monomers are exemplified. These compounds may be mono-functional or poly-functional. For example, ethylenically unsaturated acid compounds, aliphatic and aromatic functional group-containing (meth)acrylates, and amide monomers of unsaturated carboxylic acid and aliphatic polyvalent amine compounds are exemplified. As the specific examples, the compounds disclosed in JP-A-2005-29725, paragraphs [0019] to [0026] can be used.

Further, as the radically polymerizable compound, those described in JP-A-2005-29725, paragraph [0027] (polyisocyanate compounds), paragraph [0028] (urethane acrylates), [0030] (monomers containing phosphorus), and the compounds described in paragraphs [0031] and [0032] as commercially available products, can be used.

Further, those described as photo-crosslinking monomers and oligomers in Nippon Setchaku Kyokaishi (Bulletin of Japan Adhesive Association), Vol. 20, No. 7, pages 300 to 330 can also be used.

The cationically polymerizable compound is a compound the polymerization of which is initiated by the acid generated by a two-photon absorption compound and a cationic polymerization initiator and, for example, the compounds described in J. V. Crivello, Chemtech. October, page 624 (1980), JP-A-62-149784, and Nippon Setchaku Kyokaishi (Bulletin of Japan Adhesive Association), Vol. 26, No. 5, pages 179 to 187 (1990) are exemplified.

Preferred cationic compounds are compounds having at least one oxirane ring, oxetane ring or vinyl ether portion in the molecule, and more preferably compounds having an oxirane ring. Specifically, the following cationically polymerizable monomers and prepolymers (e.g., dimers, oligomers, etc.) thereof are exemplified.

The specific examples of cationically polymerizable monomers having an oxirane ring are disclosed in JP-A-2005-29725, paragraphs [0035] and [0036].

As the specific examples of cationically polymerizable monomers having an oxetane ring, the above specific examples of the cationically polymerizable monomers having an oxirane ring in which the oxirane ring is replaced with an oxetane ring are exemplified. Specifically, the compounds disclosed in JP-A-2005-29725, paragraph are exemplified.

(Polymerization Initiator)

Polymerization initiators are described in the next place. The polymerization initiators in the invention are compounds capable of generating radicals or acids (a Brønsted acid or a Lewis acid) by carrying out energy transfer or electron transfer (donating electrons or receiving electrons) from the excited state of a two-photon absorption compound generated by non-resonant two-photon absorption to thereby initiate polymerization of a polymerizable compound.

The polymerization initiators in the invention are preferably any of a radical polymerization initiator capable of generating a radical and initiating radical polymerization of a polymerizable compound, a cationic polymerization initiator capable of generating an acid alone without generating a radical and initiating cationic polymerization alone of a polymerizable compound, and a polymerization initiator capable of generating both radical and acid and initiating both radical polymerization and cationic polymerization.

As polymerization initiators, the following fourteen systems of initiators are preferably exemplified. Incidentally, these polymerization initiators may be used as mixture of two or more kinds in an arbitrary proportion, if necessary.
1) Ketone-based polymerization initiators
2) Organic peroxide-based polymerization initiators
3) Bisimidazole-based polymerization initiators
4) Trihalomethyl-substituted triazine-based polymerization initiators
5) Diazonium salt-based polymerization initiators
6) Diaryl iodonium salt-based polymerization initiators
7) Sulfonium salt-based polymerization initiators
8) Borate-based polymerization initiators
9) Diaryl iodonium-organic boron complex-based polymerization initiators
10) Sulfonium-organic boron complex-based polymerization initiators
11) Metal allene complex-based polymerization initiators
12) Sulfonate-based polymerization initiators As preferred examples of the above polymerization initiators, the following can be referred to: JP-A-2005-29725, paragraphs [0117] to [0120] (ketone-based polymerization initiators), ditto, paragraph [0122] (organic peroxide-based polymerization initiators), ditto, paragraphs [0124] to [0125] (bisimidazole-based polymerization initiators), ditto, paragraphs [0127] to [0130] (trihalomethyl-substituted triazine-based polymerization initiators), ditto, paragraphs [0132] to [0135] (diazonium salt-based polymerization initiators), ditto, paragraphs [0137] to [0140] (diaryl iodonium salt-based polymerization initiators), ditto, paragraphs [0142] to [0145] (sulfonium salt-based polymerization initiators), ditto, paragraphs [0147] to [0150] (borate-based polymerization initiators), ditto, paragraphs [0153] to [0157] (diaryl iodonium-organic boron complex-based polymerization initiators), ditto, paragraphs [0159] to [0164] (sulfonium-organic boron complex-based polymerization initiators), ditto, paragraph [0179] (metal allene complex-based polymerization initiators), and ditto, paragraphs [0181] to [0182] (sulfonate-based polymerization initiators).

13) Other Polymerization Initiators

As polymerization initiators other than the above 1) to 12), organic azide compounds such as 4,4'-diazidochalcone, aromatic carboxylic acids such as N-phenylglycine, polyhalogen compounds ($CI_4$, $CHI_S$, $CBrCl_3$), phenylisooxazolone, silanol-aluminum complexes, and aluminate complexes as disclosed in JP-A-3-209477 are exemplified.

The polymerization initiators in the invention can be classified into the following a), b) and c).
a) Polymerization initiators capable of activating radical polymerization
b) Polymerization initiators capable of activating cationic polymerization alone
c) Polymerization initiators capable of activating radical polymerization and cationic polymerization simultaneously "a) Polymerization initiators capable of activating radical polymerization" means polymerization initiators capable of generating radicals by carrying out energy transfer or electron transfer (donating electrons to a two-photon absorption compound or receiving electrons from a two-photon absorption compound) from the excited state of a two-photon absorption compound generated by non-resonant two-photon absorption to thereby initiate radical polymerization of a polymerizable compound.

In the above, the following systems are polymerization initiators capable of activating radical polymerization: 1) ketone-based polymerization initiators, 2) organic peroxide-based polymerization initiators, 3) bisimidazole-based polymerization initiators, 4) trihalomethyl-substituted triazine-based polymerization initiators, 5) diazonium salt-based polymerization initiators, 6) diaryl iodonium salt-based polymerization initiators, 7) sulfonium salt-based polymerization initiators, 8) borate-based polymerization initiators, 9) diaryl iodonium-organic boron complex-based polymerization initiators, 10) sulfonium-organic boron complex-based polymerization initiators, 11) metal allene complex-based polymerization initiators, and 12) sulfonate-based polymerization initiators.

As polymerization initiators capable of activating radical polymerization, preferred are 1) ketone-based polymerization initiators, 3) bisimidazole-based polymerization initiators, 4) trihalomethyl-substituted triazine-based polymerization initiators, 6) diaryl iodonium salt-based polymerization initiators, and 7) sulfonium salt-based polymerization initiators, and more preferred are 3) bisimidazole-based polymerization initiators, 6) diaryl iodonium salt-based polymerization initiators, and 7) sulfonium salt-based polymerization initiators.

Polymerization initiators capable of activating cationic polymerization alone are polymerization initiators capable of generating acids (a Brønsted acid or a Lewis acid) without generating radicals by carrying out energy transfer or electron transfer from the excited state of a two-photon absorption compound generated by non-resonant two-photon absorption to thereby initiate cationic polymerization of a polymerizable compound by the acids.

Of the above systems, 12) sulfonate-based polymerization initiators are polymerization initiators capable of activating cationic polymerization alone.

As cationic polymerization initiators, the compounds described in, for example, compiled by S. Peter Pappas, UV Curing, Science and Technology, pp. 23-76, A Technology Marketing Publication, and B. Klingert, M. Riediker and A. Roloff, Comments Inorg. Chem., Vol. 7, No. 3, pp. 109-138 (1988) can also be used.

Polymerization initiators capable of activating radical polymerization and cationic polymerization simultaneously are polymerization initiators capable of generating radicals or acids (a Brønsted acid or a Lewis acid) at the same time by carrying out energy transfer or electron transfer from the excited state of a two-photon absorption compound generated by non-resonant two-photon absorption to thereby initiate radical polymerization of a polymerizable compound by the generated radicals and cationic polymerization of a polymerizable compound by the generated acids, respectively.

Of the above systems, 4) trihalomethyl-substituted triazine-based polymerization initiators, 5) siazonium salt-based polymerization initiators, 6) diaryl iodonium salt-based polymerization initiators, 7) sulfonium salt-based polymerization initiators, and 11) metal allene complex-based polymerization initiators are polymerization initiators capable of activating radical polymerization and cationic polymerization at the same time.

Preferred polymerization initiators capable of activating radical polymerization and cationic polymerization at the same time are 6) diaryl iodonium salt-based polymerization initiators and 7) sulfonium salt-based polymerization initiators.

Materials capable of modulating a refractive index by polymerization are disclosed in detail in JP-A-2005-29725.

[Materials Capable of Modulating a Refractive Index by Polymerization of a Dye Having a Polymerizable Group]

The materials capable of modulating a refractive index by polymerization of a dye having a polymerizable group (also referred to as a dye monomer) can be used.

(Dye Monomer)

"Dye" in a dye monomer is a compound absorbing any of UV ray of the wavelength of 300 to 2,000 nm, visible ray, and infrared ray, preferably compounds absorbing UV ray of the wavelength of 330 to 700 nm or visible ray, and more preferably compounds absorbing visible ray of the wavelength of 400 to 700 nm. At that time, the molar extinction coefficient in that region is preferably 5,000 or more, more preferably 10,000 or more, and most preferably 20,000 or more.

When a dye monomer is used, it is preferred to use at least a sensitizing dye, a polymerization initiator, and a polymerizable compound having a binder and not having a dye portion, in addition to the dye monomer. As the polymerization initiator and polymerizable compound not having a dye portion, the same compounds as described above can be exemplified.

When a dye monomer is used, the excited state of a two-photon absorption compound generated by absorbing a light by irradiation with a two-photon recording light activates a polymerization initiator by electron transfer or energy transfer to cause polymerization of the dye having a polymerizable group and a polymerizable compound not having a dye portion. At that time at the irradiated part with light, the dye having a polymerizable group and the polymerizable compound not having a dye portion are mainly moved, and the refractive index is modulated by relegation of the binder to an unirradiated part, thereby recording pits are recorded.

Accordingly, in this case, it is preferred that the refractive index at the readout wavelength of the dye having a polymerizable group is greater than that of the binder.

In general, the refractive index of a dye takes a high value in the region from the vicinity of the absorption maximum wavelength ($\lambda$max) to the longer wavelength, in particular, it takes a very high value in the region from $\lambda$max to the wavelength of 200 nm or so longer than $\lambda$max, as high as exceeding 2 or 2.5 or more depending upon the dye.

On the other hand, the refractive index of an organic compound such as a binder polymer, not a dye, is generally 1.4 to 1.6 or so.

Therefore, this case is advantageous from the point of sensitivity improvement, since a high refractive index dye is used for modulation of refractive index. Further, for increasing sensitivity, a dye having a polymerizable group has $\lambda$max shorter than hologram readout wavelength by 10 to 200 nm preferably at the absorption spectrum, more preferably has $\lambda$max shorter by 30 to 130 nm. $\in$ is preferably 10,000 or more, and more preferably 20,000.

Further, when a polymerizable compound not having a dye portion is used, it is also preferred that the refractive index at the readout wavelength of the polymerizable compound not having a dye portion is greater than that of the binder.

At this time, it is more preferred that the polymerizable compound not having a dye portion contains at least one or more of an aryl group, an aromatic heterocyclic group, a chlorine atom, a bromine atom, an iodine atom, and a sulfur atom, and the binder does not contain such a group or atom.

The polymerization reaction is preferably any of radical polymerization, cationic polymerization and anionic polymerization, and radical polymerization or cationic polymerization is more preferred.

When polymerization is performed by radical polymerization, the dye having a polymerizable group and the polymerizable compound not having a dye portion preferably have, as the polymerizable group, an ethylenically unsaturated group portion such as an acryloyl group, a methacryloyl group, a styryl group, or a vinyl group, preferably an acryloyl group or a methacryloyl group, and when polymerization is performed by cationic polymerization or anionic polymerization, they have as the polymerizable group, any of an oxirane ring, an oxetane ring, a vinyl ether group, and an N-vinylcarbazole portion, preferably an oxirane ring or an oxetane ring.

In the next place, dyes having a polymerizable group are described in detail.

As the dye portion of the dye having a polymerizable group, a cyanine dye, a squarylium cyanine dye, a styryl dye, a pyrylium dye, a merocyanine dye, an arylidene dye, an oxonol dye, an azulenium dye, a coumarin dye, a ketocoumarin dye, a styrylcoumarin dye, a pyran dye, a xanthene dye, a thioxanthene dye, a phenothiazine dye, a phenoxazine dye, a phenazine dye, a phthalocyanine dye, an azaporphyrin dye, dye, a porphyrin dye, a condensed ring aromatic dye, a perylene dye, an azomethine dye, an anthraquinone dye, a metal complex dye, and an azo dye are preferably exemplified, more preferably a cyanine dye, a squarylium cyanine dye, a styryl dye, a merocyanine dye, an arylidene dye, an oxonol dye, a coumarin dye, a xanthene dye, a phenothiazine dye, a condensed ring aromatic dye, and an azo dye are exemplified, and still more preferably a cyanine dye, a merocyanine dye, an arylidene dye, an oxonol dye, a coumarin dye, a xanthene dye, and an azo dye are exemplified In addition to the above, dyes and dyestuffs described in, for example, compiled by Shinya Ogawara, Shikiso Handbook (Dye Handbook), published by Kodansha Ltd. (1986), compiled by Shinya Ogawara, Kinousei Shikiso no Kagaku (Chemistry of Functional Dyes) published by CMC Publishing Co., Ltd. (1981), and compiled by Chuzaburo Ikemori et al., Tokushu Kino Zairyo (Special Functional Materials), published by CMC Publishing Co., Ltd. (1986) can also be used as the dye portions.

Concerning the dye having a polymerizable group, the polymerizable groups are as described above. The polymerizable group may be substituted anywhere in the dye.

The specific examples of the dyes having a polymerizable group are shown below, but the invention is not restricted thereto.

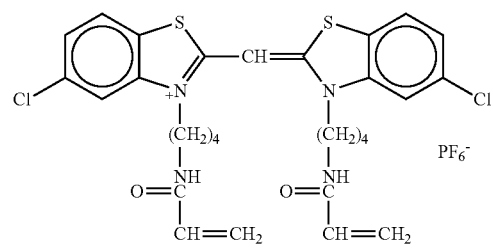

DM-1

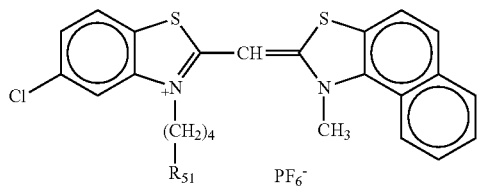

DM-2

| | $R_{51}$ |
|---|---|
| DM-2 | —NHCOCH=$CH_2$ |
| DM-3 | 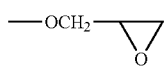 |
| DM-4 | —OCH=$CH_2$ |

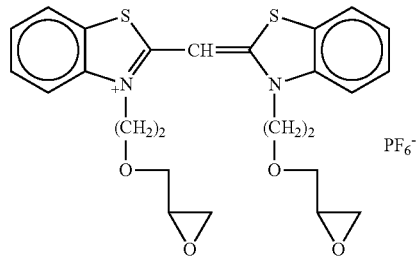

DM-5

-continued
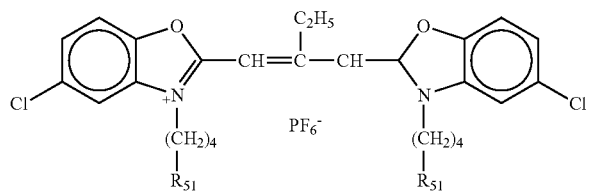
| | $R_{51}$ |
|---|---|
| DM-6 | 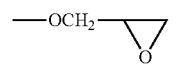 |
| DM-7 |  |
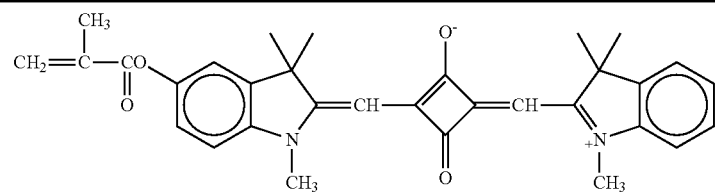
DM-8
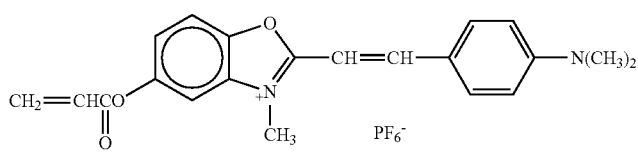
DM-9
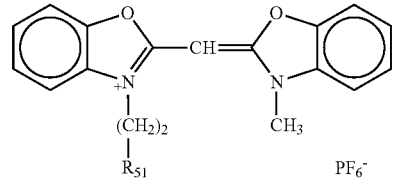
| | $R_{51}$ |
|---|---|
| DM-10 | 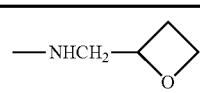 |
| DM-11 | 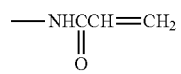 |
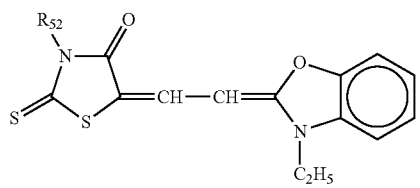
| | $R_{52}$ |
|---|---|
| DM-12 |  |
| DM-13 |  |
| DM-14 | 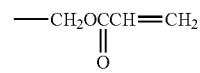 |

-continued
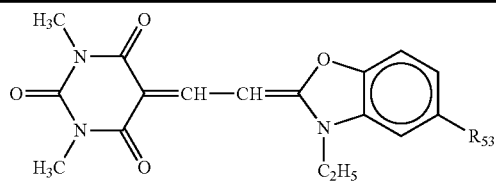
| | $R_{53}$ |
|---|---|
| DM-15 | —OC(=O)CH=CH$_2$ |
| DM-16 | —OCH$_2$-（oxirane） |
| DM-17 | —OCH$_2$-（oxetane） |
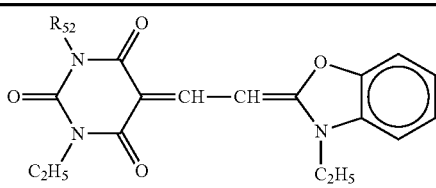
| | $R_{52}$ |
|---|---|
| DM-18 | —CH=CH$_2$ |
| DM-19 | —CH$_2$-（oxirane） |
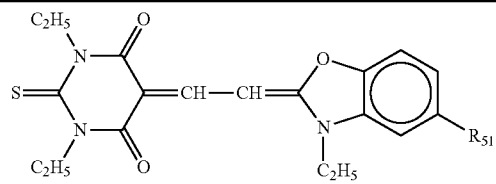
| | $R_{51}$ |
|---|---|
| DM-20 | —OC(=O)CH=CH$_2$ |
| DM-21 | —OCH$_2$-（oxirane） |
DM-22
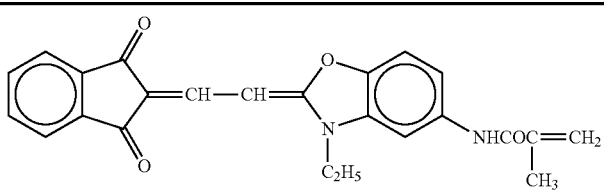
DM-23
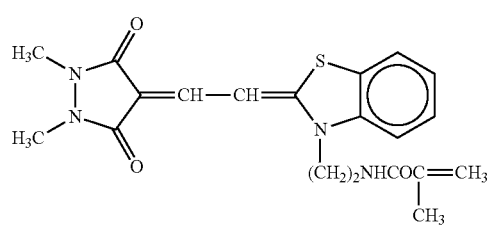

-continued
| | |
|---|---|
| 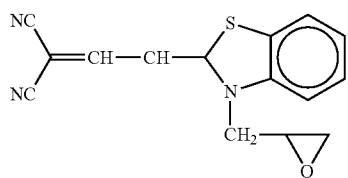 | DM-24 |
| 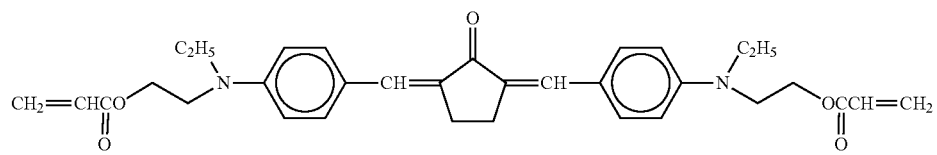 | DM-25 |
| 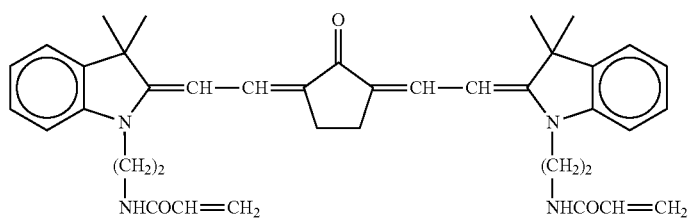 | DM-26 |
| 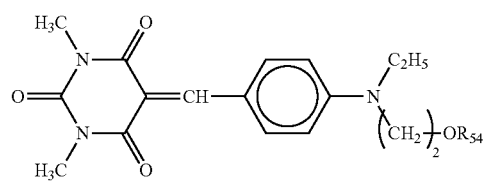 | |
| | $R_{54}$ |
|---|---|
| DM-27 | 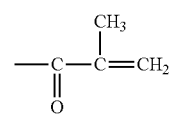 |
| DM-28 | 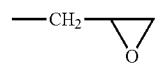 |
| DM-29 | 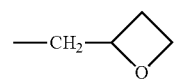 |
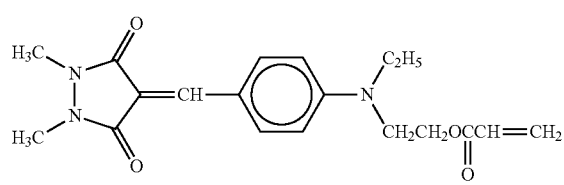 DM-30
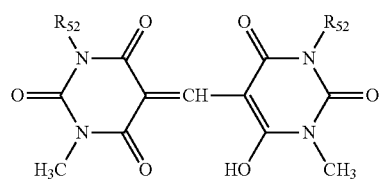

-continued
|  | $R_{52}$ |
|---|---|
| DM-31 | —CH=CH$_2$ |
| DM-32 | —(CH$_2$)$_2$OC(=O)C(CH$_3$)=CH$_2$ |
| DM-33 | —(CH$_2$)$_2$OCH$_2$—(oxirane) |
| DM-34 | —(CH$_2$)$_2$OCH$_2$—(oxetane) |
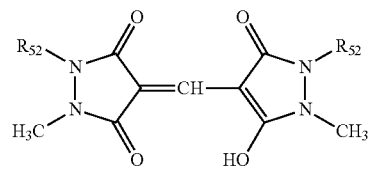
|  | $R_{52}$ |
|---|---|
| DM-35 | —CH=CH$_2$ |
| DM-36 | —(CH$_2$)$_2$OC(=O)CH=CH$_2$ |
| DM-37 | —(CH$_2$)$_3$OCH$_2$—(oxirane) |
-continued
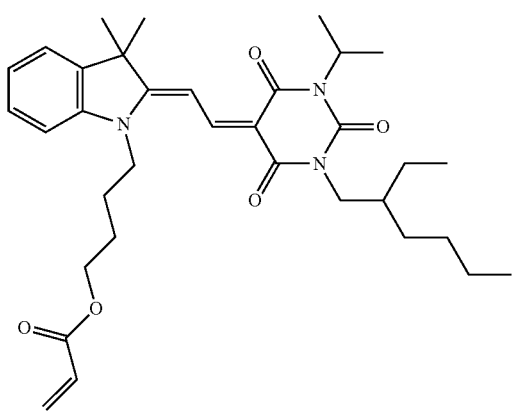
M-1
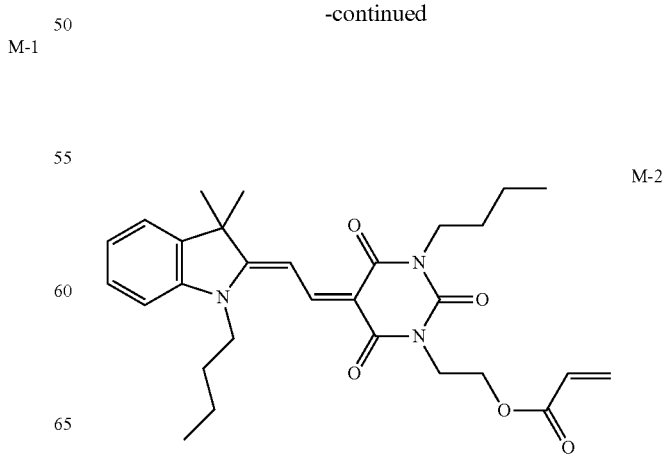
M-2

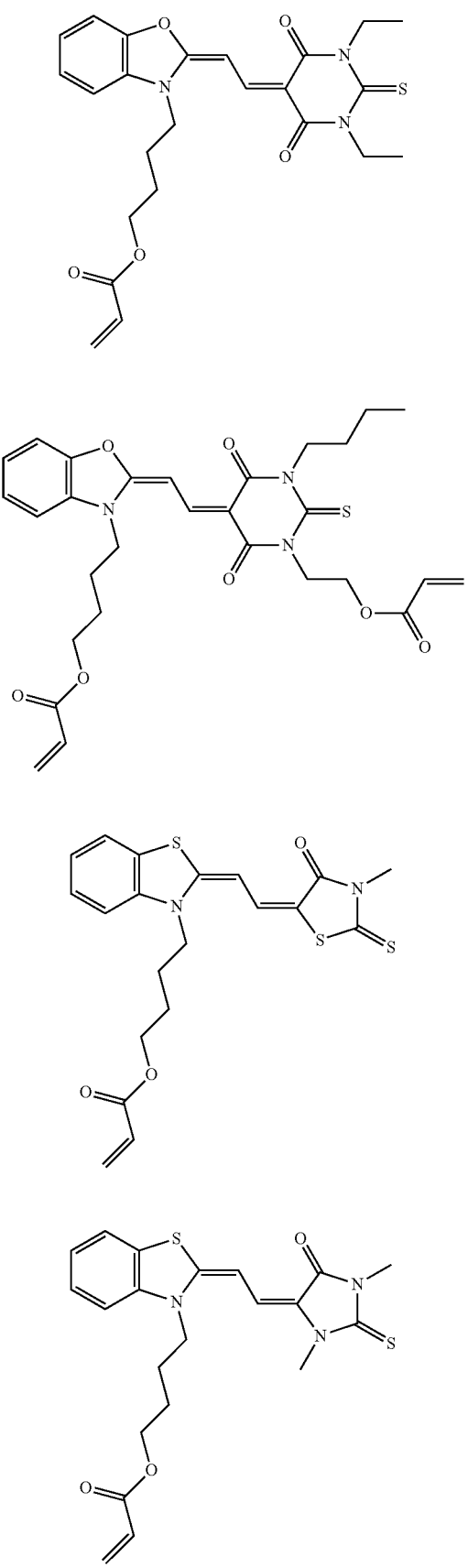
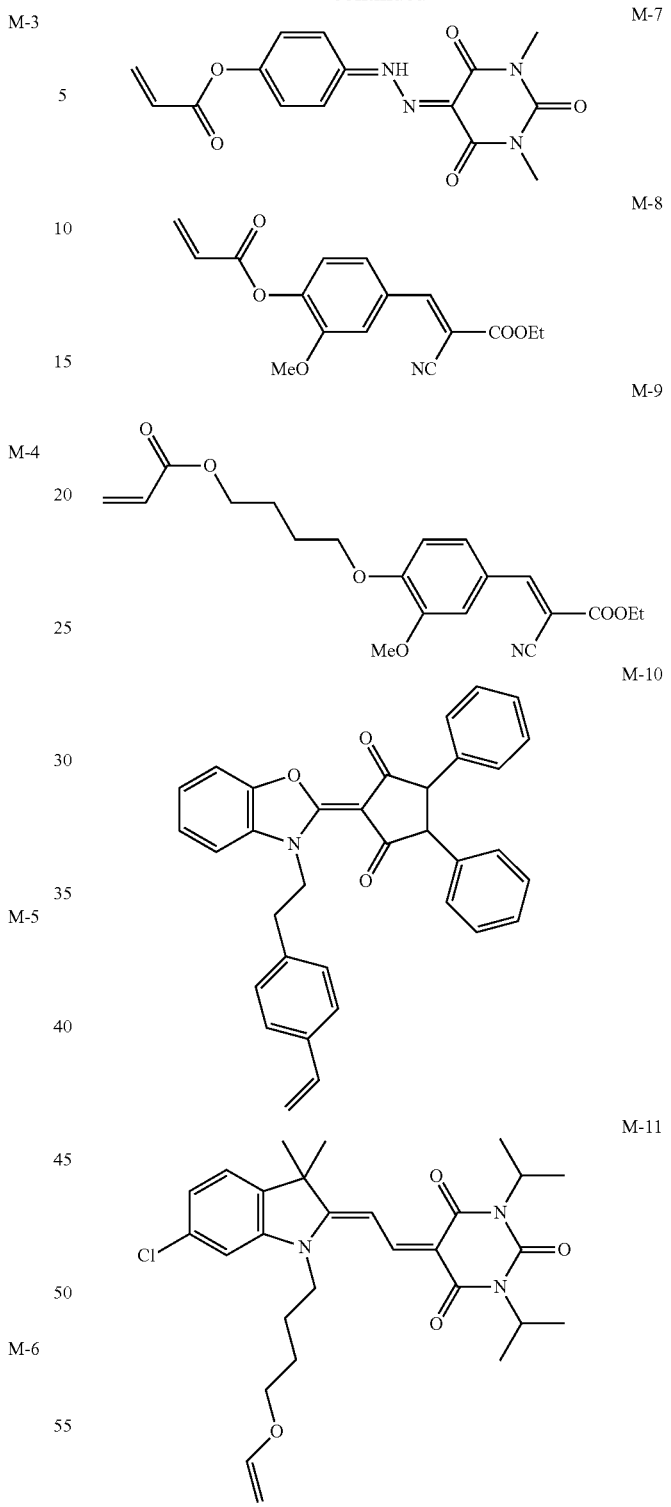

(Binder)

A binder is usually used in combination with the dye monomer for the purpose of improving the film-forming property of the composition before polymerization, uniformity of a film thickness, and preservation stability. The binder preferably has good compatibility with a polymerizable compound, a polymerization initiator and a two-photon absorption compound.

Solvent-soluble thermoplastic polymers are preferred as the binder and they can be used alone or two or more kinds may be used in combination.

As described above, the binder used in combination with the dye monomer is preferably different from the polymerizable compound in refractive index. The refractive index of the binder may be greater or the refractive index of the polymerizable compound may be greater, but it is more preferred that the refractive index of the polymerizable compound is greater than that of the binder.

For that purpose, it is preferred that either the polymerizable compound or the binder contains at least one of an aryl group, an aromatic heterocyclic group, a chlorine atom, a bromine atom, an iodine atom, and a sulfur atom, and the other one does not contain such a group or atom, and more preferably the polymerizable compound contains at least one of an aryl group, an aromatic heterocyclic group, a chlorine atom, a bromine atom, an iodine atom, and a sulfur atom, and the binder does not contain such a group or atom.

Preferred examples of the binders in the case where the refractive index of the polymerizable compound is greater than the refractive index of the binder are shown below.

The preferred examples of low refractive index binders include acrylates and α-alkyl acrylate esters and acidic polymers and interpolymers thereof (e.g., polymethyl methacrylate, polyethyl methacrylate, and copolymers of methyl methacrylate with other alkyl(meth)acrylate), polyvinyl esters (e.g., polyvinyl acetate, polyvinyl acetate/acrylate, polyvinyl acetate/methacrylate, and hydrolysis type polyvinyl acetate), ethylene/vinyl acetate copolymers, saturated or unsaturated polyurethanes, butadiene and isoprene polymers and copolymers, high molecular weight polyethylene oxides of polyglycol having a weight average molecular weight of about 4,000 to 1,000,000, epoxides (e.g., epoxide having an acrylate or methacrylate group), polyamides (e.g., N-methoxymethyl polyhexamethylene adipamide), cellulose esters (e.g., cellulose acetate, cellulose acetate succinate, and cellulose acetate butyrate), cellulose ethers (e.g., methyl cellulose, ethyl cellulose, and ethylbenzyl cellulose), polycarbonates, polyvinyl acetals (e.g., polyvinyl butyral and polyvinyl formal), polyvinyl alcohols, polyvinyl pyrrolidones, acid-containing polymers and copolymers disclosed in U.S. Pat. Nos. 3,458,311 and 4,273,857, and amphoteric polymer binders disclosed in U.S. Pat. No. 4,293,635, and more preferably cellulose acetate butyrate polymers, cellulose acetate lactate polymers, polymethyl methacrylate, acryl-based polymers and interpolymer containing methyl methacrylate/methacrylic acid and methyl methacrylate/acrylic acid copolymers, terpolymers of methyl methacrylate/C2-C4 alkyl acrylate or methacrylate/acrylic acid or methacrylic acid, polyvinyl acetate, polyvinyl acetal, polyvinyl butyral, polyvinyl formal, and mixtures thereof.

Fluorine atom-containing polymers are also preferred as the low refractive index binder. Preferred polymers are organic solvent-soluble polymers containing fluoroolefin as the essential component and containing, as the copolymerization component, one or two or more unsaturated monomers selected from alkyl vinyl ether, alicyclic vinyl ether, hydroxyl vinyl ether, olefin, haloolefin, unsaturated carboxylic acid and ester thereof, and vinyl carboxylate. Preferably the polymers have a mass average molecular weight of 5,000 to 200,000 and a fluorine atom content of 5 to 70% by mass.

As the fluoroolefins in the fluorine atom-containing polymers, tetrafluoro-ethylene, chlorotrifluoroethylene, vinyl fluoride, and vinylidene fluoride are used. As for other copolymerization components, the examples of the alkyl vinyl ethers include ethyl vinyl ether, isobutyl vinyl ether, and n-butyl vinyl ether, the examples of the alicyclic vinyl ethers include cyclohexyl vinyl ether and derivatives thereof, the examples of the hydroxyvinyl ether include hydroxybutyl vinyl ether, the examples of the olefins and haloolefins include ethylene, propylene, isobutylene, vinyl chloride and vinylidene chloride, the examples of the vinyl carboxylates include vinyl acetate and vinyl n-butyrate, and the examples of the unsaturated carboxylic acids and esters thereof include unsaturated carboxylic acid such as (meth)acrylic acid and crotonic acid, alkyl(meth)acrylate having a carbon number of 1 to 18, such as methyl(meth)acrylate, ethyl(meth)acrylate, propyl(meth)acrylate, isopropyl(meth)acrylate, butyl(meth)acrylate, hexyl(meth)acrylate, octyl(meth)acrylate, and lauryl(meth)acrylate, hydroxyalkyl(meth)acrylate having a carbon number of 2 to 8, such as hydroxyethyl(meth)acrylate and hydroxypropyl(meth)acrylate, and N,N-dimethylaminoethyl(meth)acrylate and N,N-diethyl-aminoethyl(meth)acrylate. These radically polymerizable monomers may be used alone, or two or more monomers may be used in combination. Further, if necessary, a part of the monomers may be replaced with other radically polymerizable monomer, e.g., a vinyl compound such as styrene, α-methylstyrene, vinyl toluene, or (meth)acrylonitrile. As other monomer derivatives, carboxylic acid group-containing fluoroolefin, and glycidyl group-containing vinyl ether can also be used.

As the specific examples of the fluorine atom-containing polymers, e.g., organic solvent-soluble "Lumiflon" series (e.g., Lumiflon LF200, weight average molecular weight: about 50,000, manufactured by Asahi Glass Co., Ltd.) having a hydroxyl group can be exemplified. In addition, organic solvent-soluble fluorine atom-containing polymers are commercially available from Daikin Industries Ltd., Central Glass Co., Ltd. and Pennwalt Limited, and these products can also used.

Many of these binders form a non-three-dimensional crosslinking structure. Binders forming a three-dimensional crosslinking structure are described in the next place.

(Binders Forming a Three-Dimensional Crosslinking Structure)

Many of the above binders form a non-three-dimensional crosslinking structure and binders having the structure forming a three-dimensional crosslinking structure can also be used in the optical recording material of the invention. Binders having the structure forming a three-dimensional crosslinking structure are preferably used in the light of the improvement of film-forming property, film strength and recording performance. Incidentally, "binder having the structure forming a three-dimensional crosslinking structure" is called "matrix".

The above matrix contains a component to form the three-dimensional crosslinking structure and the component in the invention can contain a thermo curable compound. As the curable compound, thermal curable compounds, and optical curable compounds hardened by photo-irradiation by using catalysts and the like can be used, and thermal curable compounds are preferred.

The thermal curable matrixes for use in the invention are not especially restricted and they can be arbitrarily selected depending upon purposes. For example, urethane resins formed from isocyanate compounds and alcohol compounds, epoxy compounds formed from oxirane compounds, melamine compounds, formalin compounds, and polymers obtained by polymerization of unsaturated acid esters such as (meth)acrylic acids and itaconic acids, and polymerization of amide compounds are exemplified as such thermal curable matrixes. Of these, polyurethane matrixes formed from isocyanate compounds and alcohol compounds are especially preferred, and polyurethane matrixes formed from polyisocyanate and polyalcohol are most preferred in view of the retaining property of recording.

Polyisocyanates and polyalcohols capable of forming a polyurethane matrix are described below with reference to specific examples.

As the polyisocyanates, specifically biscyclohexylmethanediisocyanate, hexamethylenediisocyanate, phenylene-1,3-diisocyanate, phenylene-1,4-diisocyanate, 1-methoxyphenylene-2,4-diisocyanate, 1-methylphenylene-2,4-diisocyanate, 2,4-tolylenediisocyanate, 2,6-tolylenediisocyanate, 1,3-xylylenediisocyanate, 1,4-xylylenediisocyanate, biphenylene-4,4'-diisocyanate, 3,3'-dimethoxybiphenylene-4,4'-diisocyanate, 3,3'-dimethylbiphenylene-4,4'-diisocyanate, diphenylmethane-2,4'-diisocyanate, diphenylmethane-4,4'-diisocyanate, 3,3'-dimethoxydiphenylmethane-4,4'-diisocyanate, 3,3'-dimethyldiphenylmethane-4,4'-diisocyanate, naphthylene-1,5-diisocyanate, cyclobutylene-1,3-diisocyanate, cyclopentylene-1,3-diisocyanate, cyclohexylene-1,3-diisocyanate, cyclohexylene-1,4-diisocyanate, 1-methyl-cyclohexylene-2,4-diisocyanate, 1-methylcyclohexylene-2,6-diisocyanate, 1-isocyanate-3,3,5-trimethyl-5-isocyanate methylcyclohexane, cyclohexane-1,3-bis(methylisocyanate), cyclohexane-1,4-bis(methylisocyanaate), isophoronediisocyanate, dicyclohexylmethane-2,4'-diisocyanate, dicyclohexylmethane-4,4'-diisocyanate, ethylenediisocyanate, tetramethylene-1,4-diisocyanate, hexamethylene-1,6-diisocyanate, dodecamethylene-1,12-diisocyanate, phenyl-1,3,5-triisocyanate, diphenylmethane-2,4,4'-triisocyanate, diphenylmethane-2,5,4'-triisocyanate, triphenylmethane-2,4',4"-triisocyanate, triphenylmethane-4,4',4"-triisocyanate, diphenylmethane-2,4,2',4'-tetraisocyanate, diphenylmethane-2,5,2',5'-tetraisocyanate, cyclohexane-1,3,5-triisocyanate, cyclohexane-1,3,5-tris(methylisocyanate), 3,5-dimethylcyclohexane-1,3,5-tris(methylisocyanate), 1,3,5-trimethylcyclohexane-1,3,5-tris(methylisocyanate), dicyclohexylmethane-2,4,2'-triisocyanate, dicyclohexylmethane-2,4,4'-triisocyanate, lysinediisocyanate methyl ester, and prepolymers having isocyanate at both terminals obtained from reaction between a stoichiometrically excessive amount of these organic isocyanate compounds and polyfunctional active hydrogen-containing compounds are exemplified. Of these compounds, biscyclohexylmethanediisocyanate and hexamethylenediisocyanate are especially preferred. These compounds may be used alone or two or more may be used in combination.

The above polyalcohols may be used alone, or as mixture with other polyalcohols. The examples of the polyalcohols include glycols, such as ethylene glycol, triethylene glycol, diethylene glycol, polyethylene glycol, propylene glycol, polypropylene glycol, and neopentyl glycol; diols, such as butanediol, pentanediol, hexanediol, heptanediol, and tetramethylene glycol; bisphenols; compounds obtained by modifying these polyalcohols with polyethylene oxy chain or polypropylene oxy chain; and compounds obtained by modifying these polyalcohols, such as glycerin, trimethylolpropane, butanetriol, pentanetriol, hexanetriol, or decanetriol, with polyethylene oxy chain or polypropylene oxy chain.

The content of the matrix-forming component in the optical recording composition using the dye monomers is preferably 10 to 95% by mass, and more preferably 35 to 90% by mass.

[Materials Forming a Latent Image Capable of Refractive Index/Fluorescence Modulation by Color Development of a Dye]

As the materials for forming a latent image capable of refractive index/fluorescence modulation by color development of a dye, the materials containing the dye precursors which develop colors by oxidation reaction are exemplified.

The dye precursors which develop colors by oxidation reaction are not especially restricted so long as they are compounds increasing the extinction coefficient by oxidation reaction, but it is preferred to contain at least one or more compounds of leucoquinone compounds, thiazineleuco compounds, oxazineleuco compounds, phenazineleuco compounds, and leucotriarylmethane compounds.

As preferred examples of the leucoquinone compounds, thiazineleuco compounds, oxazineleuco compounds, phenazineleuco compounds, and leucotriarylmethane compounds, the above-described compounds are exemplified and they can be used.

Materials for forming a latent image capable of refractive index/fluorescence modulation by color development of a dye are described in detail in JP-A-2005-320502.

[Materials Forming a Latent Image Capable of Refractive Index/Fluorescence Modulation by Polymerization]

The materials for forming a latent image capable of refractive index modulation by polymerization comprise the following.

1) A dye precursor whose absorption is shifted from the original state to the longer wavelength side by electron transfer or energy transfer from the excited state of the two-photon absorption compound, and capable of becoming a color developer having absorption in the wavelength region where the molar extinction coefficient of linear absorption of the two-photon absorption compound is 5,000 or less,
2) A polymerization initiator capable of initiating polymerization of a polymerizable compound by electron transfer or energy transfer from the excited state of the two-photon absorption compound,
3) A polymerizable compound, and
4) A binder.

Since 2) polymerization initiators, 3) polymerizable compounds, and 4) binders are the same with the above-described compounds, "1) dye precursors whose absorption is shifted from the original state to the longer wavelength side by electron transfer or energy transfer from the excited state of the two-photon absorption compound, and capable of becoming a color developer having absorption in the wavelength region where the molar extinction coefficient of linear absorption of the two-photon absorption compound is 5,000 or less" are described in detail in this item (hereinafter also referred to as merely "dye precursor").

The dye precursors in this item are preferably dye precursors capable of becoming color developers whose absorption is shifted from the original state to the longer wavelength side by direct electron transfer or energy transfer from the excited state of the two-photon absorption compound or the color developer, or by acid or base generated by electron transfer or energy transfer from the excited state of the two-photon absorption compound or the color developer to an acid generator or a base generator.

It is preferred for the two-photon absorption optical recording material using the dye precursor in this item to be subjected to recording by refractive index modulation. That is, it is preferred that the color developer does not have or hardly has absorption at the readout light wavelength at the time of readout.

Accordingly, the dye precursor preferably becomes a color developer not having absorption at the readout light wavelength and having absorption on the wavelength side shorter than the readout light wavelength.

On the other hand, even when the color developer has absorption at the readout light wavelength, it is also preferred for the color developer to lose the absorption and sensitizing functions by decomposition of the color developer in the process of causing polymerization by exciting the latent image, or in the succeeding fixation process.

As preferred dye precursors in this item, the following combinations are exemplified.
A) A combination of at least an acid-color development type dye precursor as the dye precursor and an acid generator, and, if necessary, an acid breeding agent
B) A combination of at least a base-color development type dye precursor as the dye precursor and a base generator, and, if necessary, a base breeding agent
C) A case where the dye precursor in this item is a compound comprising an organic compound portion having a function of cutting a covalent bond by electron transfer or energy transfer with the excited state of the two-photon absorption compound or the color developer, and an organic compound portion having a characteristic to become a color developer by release, which organic compound portions are bonded by a covalent bond, or a combination of further including a base
D) A case including a compound capable of changing absorption form by reacting to electron transfer with the excited state of the two-photon absorption compound or the color developer In every case, when energy transfer mechanism from the excited state of the two-photon absorption compound or the color developer is taken, the mechanism may be either Foerster mechanism wherein energy transfer takes place from the singlet excited state of the two-photon absorption compound or the color developer, or Dexter mechanism wherein energy transfer takes place from the triplet excited state.

At that time, for the purpose of efficient energy transfer, it is preferred that the excitation energy of the two-photon absorption compound or the color developer is greater than that of the dye precursor.

On the other hand, in the case of electron transfer mechanism from the excited state of the two-photon absorption compound or the color developer, both of the mechanism wherein electron transfer takes place from the singlet excited state of the two-photon absorption compound or the color developer, and the mechanism wherein electron transfer takes place from the triplet excited state may be taken.

Further, the excited state of the two-photon absorption compound or the color developer may donate electron to or receive electron from the dye precursor, acid generator or base generator. When electron is donated from the excited state of the two-photon absorption compound or the color developer, for the purpose of efficient electron transfer, it is preferred that the energy of the orbital where excited electrons in the excited state of the two-photon absorption compound or the color developer are present (LUMO) is higher than the energy of LUMO orbital of the dye precursor, acid generator or base generator.

When the excited state of the two-photon absorption compound or the color developer receives electron, for the purpose of efficient electron transfer, it is preferred that the energy of the orbital where holes in the excited state of the two-photon absorption compound or the color developer are present (HOMO) is lower than the energy of HOMO orbital of the dye precursor, acid generator or base generator.

The preferred combinations of dye precursors are described in further detail below.

In the first place, a case where the dye precursor is an acid-color development type dye precursor and an acid generator is further contained is explained.

The acid generator is a compound capable of generating an acid by energy transfer or electron transfer from the excited state of the two-photon absorption compound or the color developer. The acid generator is preferably stable at a dark place. The acid generator in this item is preferably a compound capable of generating an acid by electron transfer from the excited state of the two-photon absorption compound or the color developer.

As the acid generators in the dye precursor in this item, preferably the following six systems are exemplified, and preferred examples are the same with the cationic polymerization initiators described above.

That is, 1) trihalomethyl-substituted triazine-based acid generators, 2) diazonium salt-based acid generators, 3) diaryl iodonium salt-based acid generators, 4) sulfonium salt-based acid generators, 5) metal allene complex-based acid generators, and 6) sulfonate-based acid generators are preferred, and more preferably 3) diaryl iodonium salt-based acid generators, 4) sulfonium salt-based acid generators and 6) sulfonate-based acid generators are exemplified.

Further, when a cationic polymerization initiator and an acid-color development type dye precursor are used at the same time, it is preferred that the same compound functions as a cationic polymerization initiator and an acid generator. Two or more acid generators may be used as mixture in an optional proportion according to necessity.

An acid-color development type dye precursor in the case where the dye precursor in this item is an acid-color development type dye precursor and further an acid generator is contained is described.

The acid-color development type dye precursor in this item is a dye precursor capable of becoming a color developer that is changed in absorption from the original state by the acid generated by the acid generator. As the acid-color development type dye precursor in this item, a compound whose absorption is shifted to the longer wavelength side by an acid is preferred, and a compound which develops a color from colorless by an acid is more preferred.

The examples of the acid-color development type dye precursors preferably include triphenylmethane-based, phthalide-based (including indolylphthalide-based, azaphthalide-based, and triphenylmethanephthalide-based), phenothiazine-based, phenoxazine-based, fluoran-based, thiofluoran-based, xanthene-based, diphenylmethane-based, chromenopyrazole-based, leucoauramine-based, methine-based, azomethine-based, rhodamine lactam-based, quinazoline-based, diazaxanthene-based, fluorene-based, and spiropyran-based compounds, and more preferably leuco dyes having a partial structure such as lactone, lactam, oxazine or spiropyran, e.g., fluoran-based, thiofluoran-based, phthalide-based, rhodamine lactam-based, and spiropyran-based compounds are exemplified. The specific examples of these compounds are disclosed, e.g., in JP-A-2002-156454 and patents cited therein, JP-A-2000-281920, JP-A-11-279328 and JP-A-8-240908.

The dyes generated from the acid-color development type dye precursors in this item are preferably a xanthenes dye, a fluoran dye and a triphenylmethane dye.

Two or more kinds of these acid-color development type dye precursors may be used as mixture in an arbitrary proportion according to necessity.

As preferred specific examples of the acid-color development type dye precursors for use in the invention, the above-described compounds are exemplified and they can be used.

When the dye precursor group in this item contains at least the acid-color development type dye precursor as the dye precursor and an acid generator, an acid breeding agent may further be contained.

The acid breeding agent is a compound which is stable when acid is not present while it decomposes and releases an acid when an acid is present, and breeds an acid with a trace amount of the acid generated by the acid breeding agent as a trigger such that the released acid decomposes another acid breeding agent to release an acid again.

As the preferred examples of the acid breeding agents, the compounds having the structures represented by any of formulae (34-1) to (34-6) in JP-A-2005-97538 are exemplified. As more preferred specific examples, the compounds shown in paragraphs [0299] to [0301] in the same document are exemplified.

Since it is preferred to perform heating at the time of acid-breeding, the reaction system is preferably subjected to heating treatment in a process of initiating polymerization by exciting a latent image, or in a fixing process different from the above process.

In the next place, a case where the dye precursor is a base-color development type dye precursor and a base generator is further contained is explained.

The base generator is a compound capable of generating a base by energy transfer or electron transfer from the excited state of the two-photon absorption compound or the color developer. The base generator is preferably stable at a dark place. The base generator in this item is preferably a compound capable of generating a base by electron transfer from the excited state of the two-photon absorption compound or the color developer.

The base generator in this item is preferably capable of breeding a Brønsted base by light, more preferably breeding an organic base, and especially preferably breeding amines as the organic base.

The preferred examples of the base generators in the dye precursor in this item are the same with the base generators described in the base generators for anionic polymerization initiators.

Further, when an anionic polymerization initiator and a base-color development type dye precursor are used at the same time, it is preferred that the same compound functions as an anionic polymerization initiator and a base generator.

Two or more base generators may be used as mixture in an optional proportion according to necessity.

A base-color development type dye precursor in the case where the dye precursor in this item is a base-color development type dye precursor and further a base generator is contained is described.

The base-color development type dye precursor in this item is a dye precursor capable of becoming a color developer that is changed in absorption from the original state by the base generated by the base generator.

As the base-color development type dye precursor in this item, a compound whose absorption is shifted to the longer wavelength side by a base is preferred, and a compound which develops a color from colorless by a base is more preferred.

As preferred specific examples of the base-color development type dye precursors in this item, the above-described compounds are exemplified and they can be used.

When the dye precursor in this item is a base-color development type dye precursor, a base breeding agent may be contained in addition to the base generator.

The base breeding agent in this item is a compound which is stable when a base is not present while it decomposes and releases a base when a base is present, and breeds a base with a trace amount of the base generated by the base breeding agent as a trigger such that the released base decomposes another base breeding agent to release a base again.

As the base breeding agent, the compounds having the structures represented by any of formulae (34-1) to (34-6) and shown in paragraph [0287] in JP-A-2005-97538 are exemplified. As more preferred specific examples, the compounds shown in paragraphs [0299] to [0301] in the same document are exemplified.

Since it is preferred to perform heating at the time of base-breeding, when a base breeding agent is used, the reaction system is preferably subjected to heating treatment in a process of initiating polymerization by exciting a latent image, or in a fixing process different from the above process.

A case where the dye precursor in this item is a compound comprising an organic compound portion having a function of cutting a covalent bond by electron transfer or energy transfer with the excited state of the two-photon absorption compound or the color developer, and an organic compound portion having a characteristic to become a color developer by release, which organic compound portions are bonded by a covalent bond, is described.

As the compounds that can be used in this item, the compound represented by formula (32) in JP-A-2005-97538, and more specifically the compounds having the structures shown in paragraphs [0326] to [0348] in the same document are exemplified.

It is also preferred for the two-photon absorption recording material of the invention to further contain a base, if necessary, for the purpose of dissociating a dissociation type dye to be generated. The base may be an organic base or inorganic base, and preferably, for example, alkylamines, anilines, imidazoles, pyridines, carbonates, hydroxide salts, carboxylates, and metal alkoxides are exemplified. Alternatively, polymers containing any of these bases are also preferably used.

A case where the dye precursor in this item is a compound capable of changing absorption form by reacting to electron transfer with the excited state of the two-photon absorption compound or the color developer is described. Compounds capable of causing the above change are generally called what is called "electro chromic compound".

The examples of electro chromic compounds preferably used as the dye precursor in this item include polypyrroles (preferably, e.g., polypyrrole, poly(N-methylpyrrole), poly(N-methylindole), and polypyrrolopyrrole), polythiophenes (preferably, e.g., polythiophene, poly(3-hexylthiophene), polyisothianaphthene, polydithienothiophene, and poly(3,4-ethylenedioxy)thiophene), polyaniline (preferably, e.g., polyaniline, poly(N-naphthylaniline), poly(o-phenylenediamine), poly(aniline-m-sulfonic acid), poly(-methoxyaniline), poly(o-aminophenol), poly(diarylamine), poly(N-vinylcarbazole), Co-pyridinoporphyrazine complex, Ni phenanthroline complex, and Fe basophenanthroline complex.

In addition, electro chromic materials such as viologens, polyviologens, lanthanoid diphthalocyanines, styryl dyes, TNF's, TCNQ/TTF complexes, and Ru trisbipyridyl complexes are also preferred.

Further, when the dye precursor is a compound capable of changing absorption form by reacting to electron transfer with the excited state of the two-photon absorption compound or the color developer, the dye precursor in this item is preferably at least a compound having the structure represented by formula (37) in JP-A-2005-97538, more specifically the compounds as in paragraph [0352] in the same document. As preferred specific examples, the compounds in paragraph [0354] in the same document are exemplified.

The dye precursors in this item are commercially available, but they can also be synthesized by known methods.

In the two-photon absorption optical recording material, an electron-donating compound having a property of reducing the radical cation of the two-photon absorption compound or color developer, or an electron-accepting compound having a property of oxidizing the radical anion of the two-photon absorption compound or color developer can be preferably used. The use of electron-donating compound is more preferred in the point of improving color developing speed.

As preferred examples of the electron-donating compound for use in the invention, the compounds shown in JP-A-2005-97538, paragraph [0357], and the compounds shown above as the compounds which can be used in "the materials capable of modulating a refractive index or fluorescence by color development of a dye or a fluorescent dye" are exemplified. On the other hand, as preferred examples of the electron-accepting compounds for use in the invention, the compounds shown in the paragraph [0358] in the same document, and JP-A-2007-87532, paragraphs [0199] to [0212] are exemplified.

The oxidation potential of the electron-donating compound is preferably baser (on the minus side) than the oxidation potential of the two-photon absorption compound or the color developer, or baser than the reduction potential of the excited state of the two-photon absorption compound or the color developer, and the reduction potential of the electron-accepting compound is preferably nobler (on the plus side) than the reduction potential of the two-photon absorption compound or the color developer, or nobler than the oxidation potential of the excited state of the two-photon absorption compound or the color developer.

As for materials forming a latent image capable of refractive index/fluorescence modulation by polymerization, JP-A-2005-97538 can be referred to.

(Other Components)

A binder can further be used in the two-photon absorption optical recording material of the invention. The polymer matrixes for use in the polymer composition in the invention are not especially restricted, and they may be organic polymer compounds or inorganic compounds. As organic polymer compounds, solvent-soluble thermoplastic polymers are preferred and they can be used alone or in combination. They are preferably compatible with various components to be dispersed in the polymer composition.

As the binders to be used in the recording material of the invention, all of preferred examples of binders that can be used in the item of "materials capable of modulating a refractive index by polymerization of a dye having a polymerizable group" can be used. As other specific examples, the compounds disclosed in JP-A-2005-320502, paragraph [0022], i.e., acrylates and α-alkyl acrylate esters and acidic polymers and interpolymers thereof, polyvinyl esters, ethylene/vinyl acetate copolymers, saturated or unsaturated polyurethanes, butadiene and isoprene polymers and copolymers, high molecular weight polyethylene oxides of polyglycol, epoxy compounds, cellulose esters, cellulose ethers, polycarbonates, norbornene-based polymers, polyvinyl acetals, polyvinyl alcohols, and polyvinyl pyrrolidones are exemplified. As further examples, the compounds described in the same paragraph, i.e., polystyrene polymers and copolymers thereof, polymers manufactured from the reaction product of polymethylene glycol of copolyesters and aromatic acid compounds and mixtures thereof, poly-N-vinylcarbazole and copolymers thereof, and carbazole-containing polymers are exemplified. Further, the fluorine atom-containing polymers described in paragraphs [0023] to [0024] of the same document are also exemplified as preferred specific examples.

As the binders for use in the invention, acrylates and α-alkyl acrylate esters, polystyrene, polyalkylstyrene, and polystyrene copolymers are preferred, and acrylates and α-alkyl acrylates, polystyrene, and polystyrene copolymers are preferred in the point of the improvement of detecting sensitivity. As the specific examples of these compounds, acrylates and α-alkyl acrylate esters include methyl(meth)acrylate, ethyl(meth)acrylate, propyl(meth)acrylate, butyl(meth)acrylate, isobutyl(meth)acrylate, pentyl(meth)acrylate, hexyl(meth)acrylate, octyl(meth)acrylate, 2-ethylhexyl(meth)acrylate, lauryl(meth)acrylate, stearyl(meth)acrylate, and cyclohexyl(meth)acrylate, and (meth)acrylate having a benzene ring include benzyl(meth)acrylate, phenoxyethyl(meth)acrylate, phenoxypolyethylene glycol(meth)acrylate, and nonylphenol ethylene oxide adduct (meth)acrylate. Especially preferred (meth)acrylate having a benzene ring are benzyl(meth)acrylate and phenoxyethyl(meth)acrylate. These monomers may be used alone or in combination of two or more. (Meth)acrylate-based copolymers may be copolymerized with other copolymerizable monomers which are copolymerizable with alkyl(meth)acrylate, (meth)acrylate having a benzene ring, and radically polymerizable monomers containing nitrogen. The examples of such other copolymerizable monomers include alkyl vinyl ethers, e.g., allyl glycidyl ether, methyl vinyl ether, ethyl vinyl ether, isobutyl vinyl ether, n-butyl vinyl ether, 2-ethylhexyl vinyl ether, n-octyl vinyl ether, lauryl vinyl ether, cetyl vinyl ether, and stearyl vinyl ether, alkoxy alkyl (meth)acrylates, e.g., methoxyethyl (meth)acrylates and butoxyethyl (meth)acrylates, glycidyl (meth)acrylates, vinyl acetate, vinyl propionate, maleic acid (anhydride), acrylonitrile, and vinylidene chloride. Compounds having a hydrophilic polar group may be copolymerized, and as the polar groups, $-SO_3M$, $-PO(OM)_2$, and $-COOM$ (wherein M represents a hydrogen atom, alkali metal or ammonium) are exemplified.

As polyalkylstyrene compounds, polymethylstyrene, polyethylstyrene, polypropylstyrene, polybutylstyrene, polyisobutylstyrene, polypentylstyrene, hexylpolystyrene, polyoctylstyrene, poly-2-ethylhexyl styrene, polylaurylstyrene, polystearylstyrene, and polycyclohexylstyrene are exemplified, and as (meth)acrylate having a benzene ring, polybenzylstyrene, polyphenoxyethylstyrene, polyphenoxy polyethylene glycol styrene, and polynonylphenolstyrene are exemplified. The position of alkyl is preferably α-, para-position. These monomers may be used alone or in combination of two or more. Polystyrene copolymers may be copolymerized with other copolymerizable monomers which are copolymerizable with a conjugated diene compound, alkylstyrene, styrene having a benzene ring, and radically polymerizable monomers containing nitrogen. The examples of such other copolymerizable monomers include acetylene, butadiene, acrylonitrile, vinylidene chloride, polyethylene, allyl glycidyl ether, methyl vinyl ether, ethyl vinyl ether, isobutyl vinyl ether, n-butyl vinyl ether, 2-ethylhexyl vinyl ether, n-octyl vinyl ether, lauryl vinyl ether, cetyl vinyl ether, and stearyl vinyl ether.

A thermal stabilizer can be added to the two-photon absorption optical recording material of the invention for the improvement of preservation stability.

Useful thermal stabilizer include hydroquinone, phenidone, p-methoxyphenol, alkyl- and aryl-substituted hydroquinone and quinone, catechol, t-butyl catechol, pyrogallol, 2-naphthol, 2,6-di-t-butyl-p-cresol, phenothiazine and chloroanil. Dinitrosodimer described in U.S. Pat. No. 4,168,982 by Mr. Pazos is also useful.

A plasticizer can be used in the two-photon absorption optical recording material of the invention for changing adhering property, flexibility, stiffness and other mechanical characteristics of the optical recording material. As the plasticizer, triethylene glycol dicaprylate, triethylene glycol bis (2-ethylhexanoate), tetraethylene glycol diheptanoate, diethyl sebacate, dibutyl suberate, tris(2-ethylhexyl)phosphate, tricresyl phosphate and dibutyl phthalate are exemplified.

The two-photon absorption optical recording material of the invention may be prepared according to ordinary methods. For example, the material can be prepared by the above essential components and optional components as they are, or by adding a solvent, if necessary.

The examples of the solvents include ketone solvents, e.g., methyl ethyl ketone, methyl isobutyl ketone, acetone, and cyclohexanone, ester solvents, e.g., ethyl acetate, butyl acetate, ethylene glycol diacetate, ethyl lactate, and cellosolve acetate, hydrocarbon solvents, e.g., cyclohexane toluene and cylene, ether solvents, e.g., tetrahydrofuran, dioxane, and diethyl ether, cellosolve solvents, e.g., methyl cellosolve, ethyl cellosolve, butyl cellosolve, and dimethyl cellosolve, alcohol solvents, e.g., methanol, ethanol, n-propanol, 2-propanol, n-butanol, and diacetone alcohol, fluorine solvents, e.g., 2,2,3,3-tetrafluoropropanol, halogenated hydrocarbon solvents, e.g., dichloromethane, chloroform and 1,2-dichloroethane, amide solvents, e.g., N,N-dimethylformamide, and nitrile solvents, e.g., acetonitrile and propionitrile.

The two-photon absorption optical recording material of the invention can be prepared by directly coating the composition on a substrate with a spin coater, a roll coater or a bar coater, or a cast film may be laminated on a substrate according to ordinary methods to thereby obtain a two-photon absorption optical recording material.

"Substrate" means an optional natural or synthetic support, and preferably means a material capable of being present in the form of a flexible or rigid film, sheet or plate.

Preferred substrates are polyethylene terephthalate, resin-undercoated polyethylene terephthalate, polyethylene terephthalate subjected to flame treatment or electrostatic discharge treatment, cellulose acetate, polycarbonate, polymethyl methacrylate, polyester, polyvinyl alcohol and glass.

Used solvents can be removed by evaporation at drying time. Heating or reduced pressure may be used for the evaporation removal.

A protective layer may be formed on the two-photon absorption optical recording material for excluding oxygen. The protective layer of a plastic film or plate such as polyolefin, e.g., polypropylene or polyethylene, polyvinyl chloride, polyvinylidene chloride, polyvinyl alcohol, polyethylene terephthalate, or a cellophane film, may be stuck by electrostatic adhesion or lamination with an extruder, or may be coated with a solution of the above polymer. Alternatively, a glass plate may be laminated. Further, for increasing air tightness, an adhesive or a liquid substance may be present between the protective layer and the photosensitive layer and/or between the substrate and the photosensitive layer.

Furthermore, the two-photon absorption optical recording material of the invention may have a multilayer structure comprising recording layers containing recording components and non-recording layers not containing recording components laminated alternately. Due to the structure of lamination of the recording layers and non-recording layers laminated alternately, a non-recording layer intervenes between the recording layers, and extension of the recording area in the vertical direction to the recording layer surface is intercepted. Accordingly, even if the recording layer is restricted to the thickness of the wavelength order of irradiating light, it is possible to lessen crosstalk. As a result, not only the thickness of the recording layer itself can be thinned but also layer-to-layer distance including the non-recording layers can be decreased.

Since it is necessary to satisfy the amount of the refractive index change of the recording layer at recording time, and interference condition by reflected light on the obverse and reverse of the recording layer to light incidence direction, the thickness of the recording layer is, depending upon the amount of the refractive index change of the recording layer, preferably 50 nm or more and 5,000 nm or less, more preferably 100 nm or more and 1,000 nm or less, and still more preferably 100 nm or more and 500 nm or less.

The non-recording layer is a thin layer formed with a material not causing fluctuation in absorption spectrum or light emission spectrum by irradiation of the recording light.

As the materials for use in the non-recording layer, from the viewpoint of easiness in manufacture of the multilayer structure, materials soluble in solvents which do not dissolve the materials used in the recording layer are preferred, and of these materials, transparent polymer materials not having absorption in the visible light region are preferred. As such materials, water-soluble polymers are preferably used.

As the specific examples of the water-soluble polymers, polyvinyl alcohol (PVA), polyvinyl pyridine, polyethyleneimine, polyethylene oxide, polypropylene oxide, polyvinyl pyrrolidone, polyacrylamide, polyacrylic acid, sodium polyacrylate, carboxymethyl cellulose, hydroxyethyl cellulose, and gelatin can be exemplified, preferably PVA, polyvinyl pyridine, polyacrylic acid, polyvinyl pyrrolidone, carboxymethyl cellulose, and gelatin, and most preferably PVA.

When a water-soluble polymer is used as the material, the non-recording layer can be formed by dissolving the water-soluble polymer in water and coating the obtained coating solution by a coating method such as spin coating.

The thickness of the non-recording layer is, for reducing the crosstalk between recording layers sandwiching the non-recording layer, and from the viewpoints of the wavelength of the light for use in recording and readout, recording power, readout power, NA of lens, and recording sensitivity of the recording materials, preferably 1 µm or more and 50 µm or less, more preferably 1 µm or more and 20 µm or less, and still more preferably 1 µm or more and 10 µm or less.

The number of pairs of the alternately laminated recording layers and non-recording layers is preferably in the range of 9 to 200, more preferably in the range of 10 to 100, and still more preferably in the range of 10 to 30, from the viewpoints of the recording capacity required of the two-photon absorption recording medium and the aberration determined by the optics to be used.

[B] Two-Photon Absorption Recording Material Containing (a) Non-Resonant Two-Photon Absorption Compound, and (b') Polymer Binder (Hereinafter Also Referred to as "Two-Photon Absorption Recording Material [B]")

Two-photon absorption recording material [B] of the invention is provided as a recording layer on a supporting substrate, or used as a recording medium having a layer structure in contiguous to a layer having a different refractive index from that of the recording layer.

The mechanism of recording/readout of the recording medium using the two-photon absorption recording material [B] of the invention as a recording layer is not clear but it is presumed as follows.

In a recording layer using recording material [B] comprising a two-photon absorption compound and a polymer binder, heat is generated at the two-photon absorption part, and the refractive index of the recording layer changes, or the obverse of the recording layer or the supporting support or the interference between the recording layer and contiguous layer having a refractive index different from that of the recording layer changes, by which recording is performed by the change of reflectance. Readout is effected by the comparison of difference in reflectance between the place where reflectance changes by recording and the unrecorded place where the reflectance is not changed.

In a recording layer, change in reflectance is caused in a wide range in the progressing direction of a recording light (hereinafter merely "depth direction") and recording spot is recorded. At this time, refractive index change takes place depending upon the recording light intensity, so that when a light for readout is irradiated on the recorded spot at the time of readout, the recorded spot functions as a lens and the function as a lens diverts the readout light from the recorded spot or converges the readout light in the recorded spot. Accordingly, when the readout light is irradiated in conformity with the interface at the time of readout of information, the light returning from the recorded spot is weakened (when the refractive index becomes small) or strengthened (when the refractive index becomes great), and so there is caused difference in intensity between the returned light and the returned light from the interface at the non-recorded part, and information can be read out by the modulation of the difference in intensity.

As (a) non-resonant two-photon absorption compound for use in two-photon absorption recording material [B] of the invention, the same compounds as used in two-photon absorption recording material [A] are used.

As (b') polymer binder for use in two-photon absorption recording material [B], the same compounds as used in two-photon absorption recording material [A] can be used.

Two-photon absorption recording material [B] of the invention does not contain (b) recording component in which at least either refractive index or fluorescence intensity changes, which is used in two-photon absorption recording material [A].

As compared with two-photon absorption recording material [A], two-photon absorption recording material [B] of the invention is high in the content of polymer binder, and the recording sensitivity of the recording medium using recording material [B] is as high as 10 times or more as compared with the case where a recording medium using recording material [A] is recorded by fluorescence modulation system.

When a compound not having linear absorption to visible light is used as the two-photon absorption compound in two-photon absorption recording material [B] of the invention, recording material [B] and a recording medium using recording material [B] is free from exclusion of light.

Example

The invention will be described specifically with reference to specific examples on the basis of experiment results. However, the invention is by no means restricted thereto.

The synthesizing methods of Comparative Compound R-2, and Compounds D-11, D-41 and D-405 of the invention are shown below.

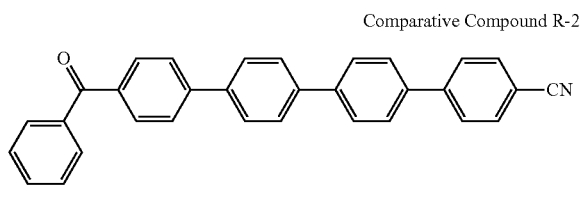 [SMILES: N#Cc1ccc(-c2ccc(-c3ccc(-c4ccc(C(=O)c5ccccc5)cc4)cc3)cc2)cc1]

Comparative Compound R-2

Synthesizing Method of Comparative Compound R-2

Comparative Compound R-2 is synthesized in the manner as shown below.

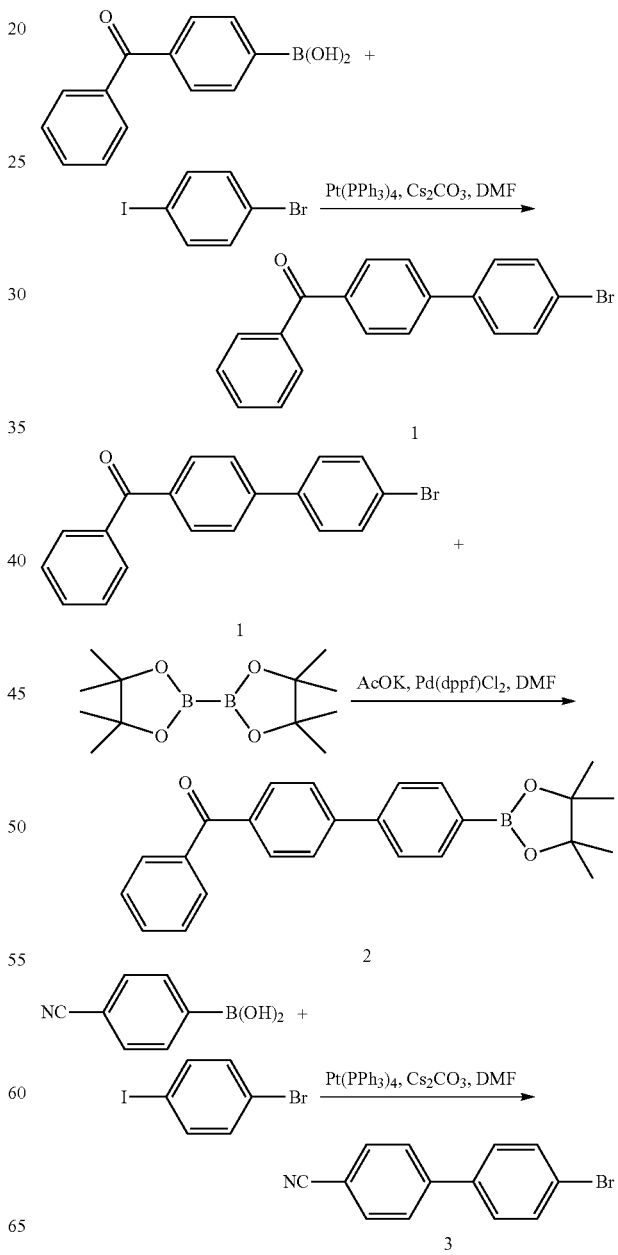

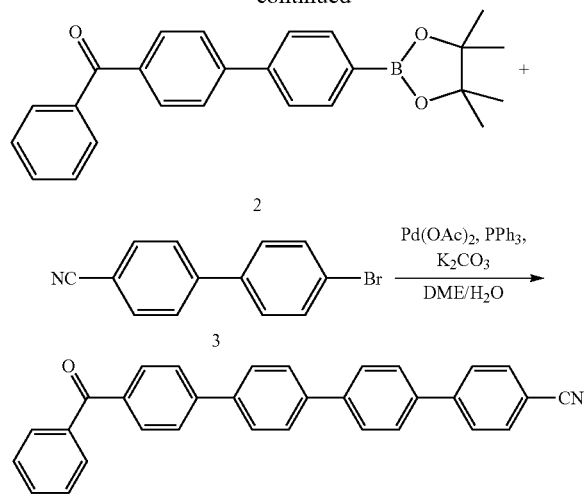

Synthesis of Raw Material Compound 1

4-Benzoylphenylboronic acid (2.7 g) (12 mmol) and 2.8 g of 1-bromo-4 iodobenzene (10 mmol) are dissolved in 50 ml of dimethyl formamide (DMF), and then 0.6 g of tetrakis(triphenylphosphine) platinum (0.5 mmol) and 6.5 g of cesium carbonate (20 mmol) are added thereto, and the reaction system is subjected to heating for 8 hour under nitrogen flow.

After the reaction solution is allowed to be cooled, distilled water and about 600 ml of ethyl acetate are added and extraction is performed. After removing an aqueous layer and separating an organic layer, the system is dried with magnesium sulfate. The filtrate from which magnesium sulfate is filtered out is evaporated to dryness in a rotary evaporator, and refined by silica gel column (ethyl acetate/hexane: 1/10) to obtain 1.6 g of colorless raw material compound 1 (yield: 48%). The obtained compound 1 is confirmed to be an objective compound by mass spectrum and $^1$H NMR spectrum.

Synthesis of Raw Material Compound 2

Raw material compound 1 (0.68 g) (2 mmol), 0.63 g of bis(pinacolato)diboron (2.5 mmol), 0.59 g of potassium acetate (6 mmol), and 100 mg of [1,1'-bis(diphenylphosphino)ferrocene]dichloropalladium (0.12 mmol) are suspended in 50 ml of DMF, and the reaction system is subjected to heating at 80° C. for 9 hour under nitrogen flow. After the reaction solution is allowed to be cooled, distilled water and ethyl acetate are added and extraction is performed. After removing an aqueous layer and separating an organic layer, the system is dried with magnesium sulfate. The filtrate from which magnesium sulfate is filtered out is evaporated to dryness in a rotary evaporator, and refined by silica gel column (ethyl acetate/hexane: 1/20) to obtain 0.65 g of colorless raw material compound 2 (yield: 85%). The obtained compound 2 is confirmed to be an objective compound by mass spectrum and $^1$H NMR spectrum.

Synthesis of Raw Material Compound 3

4-cyanobenzeneboronic acid (1.76 g) (12 mmol) and 2.8 g of 1-bromo-4 iodobenzene (10 mmol) are dissolved in 60 ml of DMF, and then 0.6 g of tetrakis(triphenylphosphine) platinum (0.5 mmol) and 6.5 g of cesium carbonate (20 mmol) are added thereto, and the reaction system is subjected to heating for 8 hour at 120° C. under nitrogen flow. After the reaction solution is allowed to be cooled, distilled water and about 600 ml of ethyl acetate are added and extraction is performed. After removing an aqueous layer and separating an organic layer, the system is dried with magnesium sulfate. The filtrate from which magnesium sulfate is filtered out is evaporated to dryness in a rotary evaporator, and refined by silica gel column (ethyl acetate/hexane: 1/10) to obtain 0.53 g of colorless raw material compound 3 (yield: 21%). The obtained compound 3 is confirmed to be an objective compound by mass spectrum and $^1$H NMR spectrum.

Synthesis of Compound R-2

Raw material compound 2 (0.5 g) (1.3 mmol) and 0.33 g of raw material compound 3 (1.3 mmol) are dissolved in a mixed solvent of 20 ml of distilled water and of 14 ml of ethylene glycol dimethyl ether, and then 14.6 mg of palladium acetate (0.065 mmol), 34 mg of triphenylphosphine (0.13 mmol), and 0.97 g of potassium carbonate (7 mmol) are added thereto, and the reaction system is refluxed with heating for 2 hour. After the reaction solution is allowed to be cooled, distilled water and dichloromethane are added and extraction is performed. After removing an aqueous layer and separating an organic layer, the system is dried with magnesium sulfate. The filtrate from which magnesium sulfate is filtered out is evaporated to dryness in a rotary evaporator to obtain a crude product. The obtained crude product is refined by sublimation to thereby obtain 0.11 g of an objective product (yield: 19%). The obtained compound is confirmed to be objective compound R-2 by mass spectrum and $^1$H NMR spectrum.

$^1$H NMR (CDCl$_3$) 7.52 (t, 2H), 7.62 (t, 1H), 7.71 (d, 2H), 7.78 (m, 12H), 7.86 (d, 2H), 7.93 (d, 2H)

Synthesizing Method of Compound D-11

Compound D-11 is synthesized in the manner as shown below.

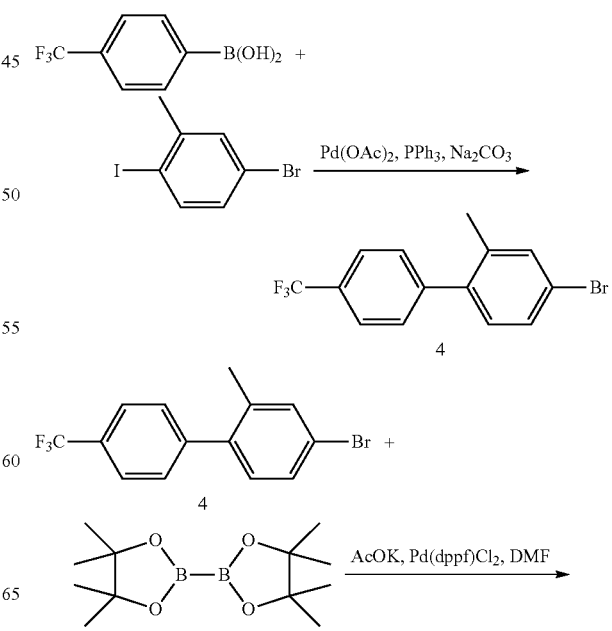

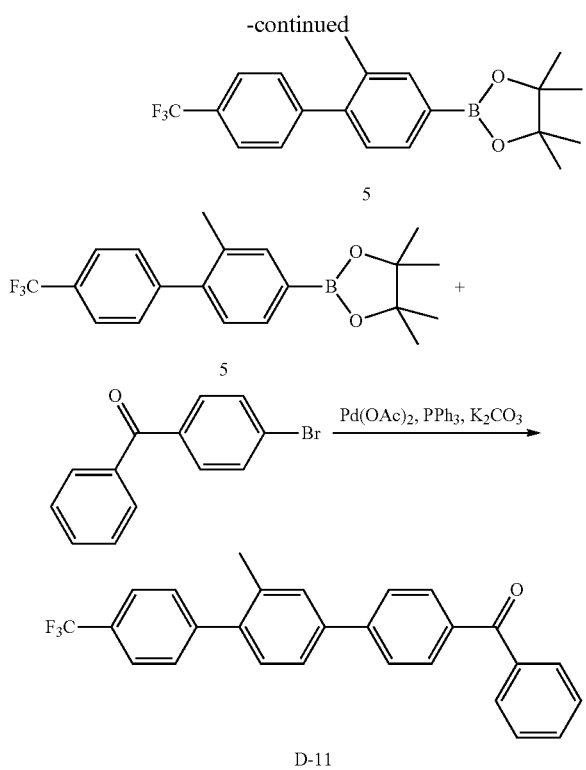

material compound 5 (yield: 54%). The obtained compound 5 is confirmed to be an objective compound by $^1$H NMR spectrum.

Synthesis of Compound D-11

Raw material compound 5 (0.8 g) (2.2 mmol) and 0.52 g of p-bromobenzophenone (2.0 mmol) are dissolved in 35 ml of ethylene glycol dimethyl ether-distilled water mixed solvent (6:1), and then 22.5 mg of palladium acetate (0.1 mmol), 52.4 mg of triphenylphosphine (0.2 mmol), and 0.64 g of potassium carbonate (6 mmol) are added thereto, and the reaction system is refluxed with heating for 2 hour. After the reaction solution is allowed to be cooled, distilled water and ethyl acetate are added and extraction is performed. After removing an aqueous layer and separating an organic layer, the system is dried with magnesium sulfate. The filtrate from which magnesium sulfate is filtered out is evaporated to dryness in a rotary evaporator to obtain a crude product. The obtained crude product is refined by silica gel column (ethyl acetate:hexane=1:100→1:5) to obtain 0.71 g of a white crystal (yield: 77%). The obtained compound is confirmed to be objective compound D-11 by mass spectrum and $^1$H NMR spectrum.

$^1$H NMR (CDCl$_3$) 2.37 (s, 3H), 7.34 (d, 1H), 7.48-7.55 (m, 7H), 7.7-7.8 (m, 4H), 7.85 (m, 2H), 7.95 (m, 2H)

Synthesis of Raw Material Compound 4 p-Trifluoromethylphenylboronic acid (6.98 g) (37 mmol), 9.92 g of 5-bromo-2-iodotoluene (33 mmol), and 10.6 g of sodium carbonate (100 mmol) are dissolved in 190 ml of ethylene glycol dimethyl ether-distilled water mixed solvent (14:5), and then 0.37 g of palladium acetate (1.7 mmol) and 0.88 g of triphenylphosphine (3.3 mmol) are added thereto, and the reaction system is subjected to heating for 7 hour under nitrogen flow.

After the reaction solution is allowed to be cooled, distilled water and about 600 ml of ethyl acetate are added and extraction is performed. After removing an aqueous layer and separating an organic layer, the system is dried with magnesium sulfate. The filtrate from which magnesium sulfate is filtered out is evaporated to dryness in a rotary evaporator, and refined by silica gel column (ethyl acetate: hexane=1:400) to obtain 10.1 g of white raw material compound 4 (yield: 96%). The obtained compound 4 is confirmed to be an objective compound by $^1$H NMR spectrum.

Synthesis of Raw Material Compound 5

Raw material compound 4 (9.5 g) (30 mmol), 9.9 g of bis(pinacolato)diboron (39 mmol), 8.8 g of potassium acetate (90 mmol), and 0.73 g of [1,1'-bis(diphenylphosphino)ferrocene]dichloropalladium (0.9 mmol) are suspended in 170 ml of DMF, and the reaction system is subjected to heating at 80° C. for 4 hour under nitrogen flow. After the reaction solution is allowed to be cooled, distilled water and ethyl acetate are added and extraction is performed. After removing an aqueous layer and separating an organic layer, the system is dried with magnesium sulfate. The filtrate from which magnesium sulfate is filtered out is evaporated to dryness in a rotary evaporator, and refined by silica gel column (ethyl acetate:hexane=1:100→1:10) to obtain 5.9 g of colorless raw Synthesizing Method of Compound D-41

Compound D-41 is synthesized in the manner as shown below.

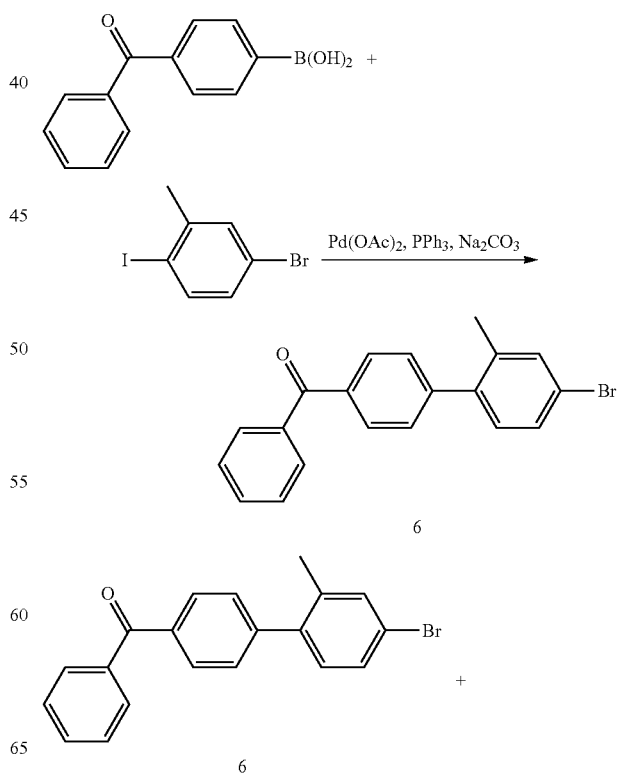

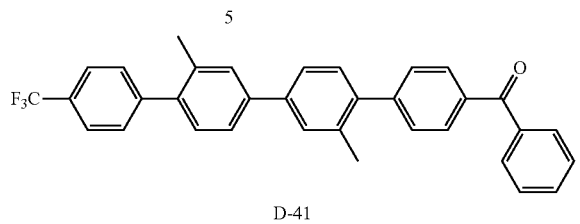

Synthesis of Raw Material Compound 6

4-Benzoylphenylboronic acid (6.25 g) (21 mmol), 5.23 g of 5-bromo-2 iodotoluene (23 mmol), and 6.68 g of sodium carbonate (63 mmol) are dissolved in 130 ml of ethylene glycol dimethyl ether-distilled water mixed solvent (10:3), and then 0.24 g of palladium acetate (1.05 mmol) and 0.55 g of triphenylphosphine (2.1 mmol) are added thereto, and the reaction system is subjected to heating for 3 hour under nitrogen flow.

After the reaction solution is allowed to be cooled, distilled water and about 600 ml of ethyl acetate are added and extraction is performed. After removing an aqueous layer and separating an organic layer, the system is dried with magnesium sulfate. The filtrate from which magnesium sulfate is filtered out is evaporated to dryness in a rotary evaporator, and refined by silica gel column (ethyl acetate: hexane=1:40→1:10) to obtain 6.6 g of white to pale yellow raw material compound 6 (yield: 90%). The obtained compound 6 is confirmed to be an objective compound by mass spectrum and $^1$H NMR spectrum.

Synthesis of Compound D-41

Raw material compound 5 (0.8 g) (2.2 mmol) and 0.70 g of raw material compound 6 (2.0 mmol) are dissolved in 25 ml of ethylene glycol dimethyl ether-distilled water mixed solvent (4:1), and then 22.5 mg of palladium acetate (0.1 mmol), 52.4 mg of triphenylphosphine (0.2 mmol), and 0.64 g of potassium carbonate (6 mmol) are added thereto, and the reaction system is refluxed with heating for 3 hour. After the reaction solution is allowed to be cooled, distilled water and ethyl acetate are added and extraction is performed. After removing an aqueous layer and separating an organic layer, the system is dried with magnesium sulfate. The filtrate from which magnesium sulfate is filtered out is evaporated to dryness in a rotary evaporator, to obtain a crude product. The obtained crude product is refined by silica gel column (ethyl acetate: hexane=1:40→1:10) to obtain 0.37 g of a white crystal (yield: 37%). The obtained compound is confirmed to be objective compound D-41 by mass spectrum and $^1$H NMR spectrum.

$^1$H NMR (CDCl$_3$) 2.38 (s, 3H), 2.41 (s, 3H), 7.3 (dxd. 2H), 7.5-7.7 (m, 11H), 7.75 (m, 2H), 7.92 (m, 4H)

Synthesizing Method of Compound D-405

Compound D-405 is synthesized in the manner as shown below.

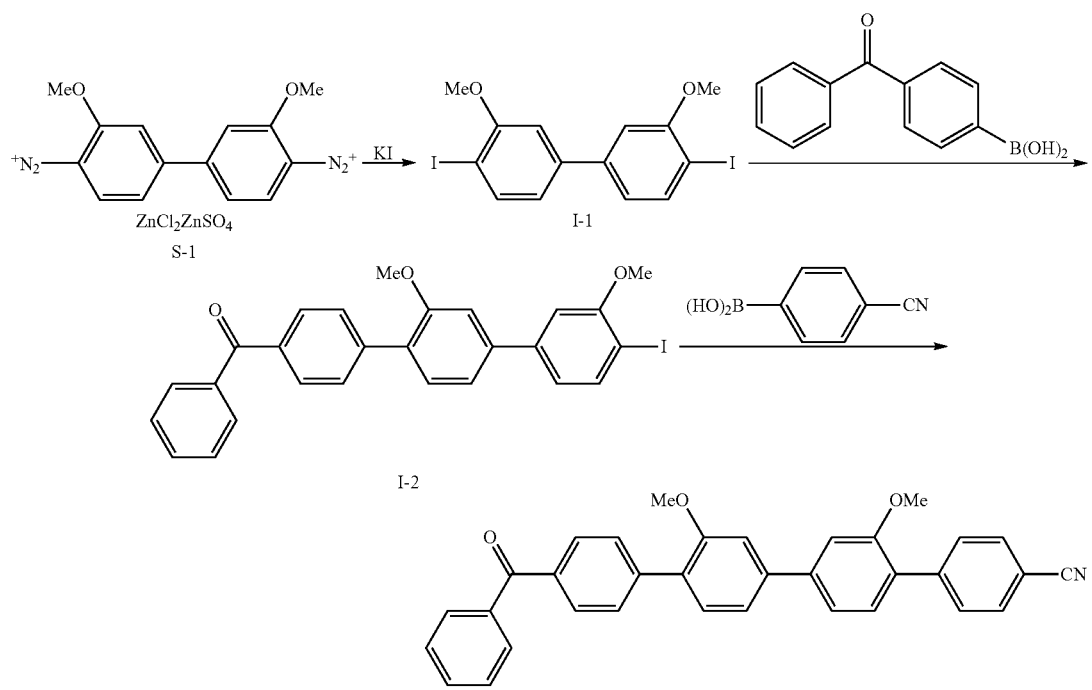

Potassium iodide (33.2 g) (200 mmol) is dissolved in 150 ml of water, and 10.0 g of raw material compound S-1 (manufactured by Sigma Aldrich) (15.7 mmol) is added to the above solution while stirring the solution in an ice bath. After stirring the solution in an ice bath for a while, stirring is further continued at room temperature. The formed product is extracted with ethyl acetate. The organic layer is washed with a 10% sodium hydroxide aqueous solution, a saturated sodium chloride aqueous solution, and a 5% sodium hydrogensulfite, dried with magnesium sulfate and evaporated to dryness. The reaction product is refined with column chromatography (eluent: ethyl acetate/hexane=⅕) to obtain 5.40 g of intermediate compound I-1 (yield: 74%) as a pale yellow solid state. The obtained I-1 (5.00 g) (10.7 mmol), 1.10 g of 4-benzoylphenylboronic acid (4.86 mmol), 0.281 g of $Pd(PPh_3)_4$ (0.243 mmol), and 2.02 g of potassium carbonate (14.6 mmol) are dissolved in 25 ml of toluene, 8 ml of ethanol and 4 ml of water, and refluxed under nitrogen flow. The reaction solution is allowed to be cooled at room temperature, and extracted with ethyl acetate. The organic layer is washed with pure water, dried with magnesium sulfate, and the desiccant is filtered out. The reaction product is subjected to evaporation to dryness, refining by column chromatography (eluent: toluene) to thereby obtain 0.780 g of intermediate compound I-2 (yield: 31%) as a pale yellow solid state. Subsequently, the obtained I-2 (0.780 g) (1.50 mmol), 661 mg of 4-cyanophenylboronic acid (4.50 mmol), 87 mg of $Pd(PPh_3)_4$ (0.075 mmol), and 829 g of potassium carbonate (6.00 mmol) are dissolved in 100 ml of toluene, 5 ml of ethanol and 3 ml of water, and refluxed under nitrogen flow. The reaction solution is allowed to be cooled at room temperature, and extracted with ethyl acetate. The organic layer is washed with brine, dried with magnesium sulfate, and the desiccant is filtered out. The reaction product is subjected to evaporation to dryness, refining by column chromatography (eluent: toluene), and then washing by stirring with ethyl acetate to thereby obtain 490 mg of a white solid (yield: 67%). The obtained compound is confirmed to be objective compound D-405 by mass spectrum and $^1$H NMR spectrum.

$^1$H NMR (400 MHz, DMSO-d6) δ 7.91-7.90 (m, 2H), 7.83-7.69 (m, 9H), 7.62-7.58 (m, 2H), 7.52-7.47 (m, 6H), 3.94 (s, 3H), 3.93 (s, 3H)

ESI Mass spectrum m/z=496.3

<Measuring Method of Two-Photon Absorption Cross-Sectional Area>

Measurement of a two-photon absorption cross-sectional area of the synthesized compound is carried out by Z scanning method described in Mansoor Sheik-Baha et al., IEEE, Journal of Quantum Electronics, 1990, 26, 760. Z scanning method is a widely used method as the measuring method of a non-linear optical constant. In the vicinity of the focus of converged laser beam, a measuring sample is moved along the beam and the change of the quantity of transmitting light is recorded. Since the power density of incident light changes depending upon the position of a sample, the quantity of transmitting light attenuates in the vicinity of the focus in the case where non-linear absorption is present. A two-photon absorption cross-sectional area is computed by fitting the change of the quantity of transmitting light to the theoretical curve predictable from the intensity of incident light, the size of converging spot of light, the thickness of a sample and the concentration of a sample. As the light sources for the measurement of a two-photon absorption cross-sectional area, a Ti-sapphire pulse laser (pulse duration: 100 fs, repetition: 80 MHz, average output: 1 W, peak power: 100 kW) obtained by combining a readout amplifier and light parametric amplifier is used. As the sample for the measurement of two-photon absorption cross-sectional area, a solution obtained by dissolving each compound in chloroform in concentration of $1\times10^{-5}$.

<Evaluation of Two-Photon Absorption Cross-Sectional Area>

Two-photon absorption cross-sectional areas of the compounds of the invention D-11, D-41, D-42 and D-405 and the compound described in Y. Morel, O. Stephan, C. Andraud, and P. L. Baldeck, Synth. Met. 2001, 124, 237 (comparative compound R-1 shown below), and comparative compound R-2 are shown in Table 1 below.

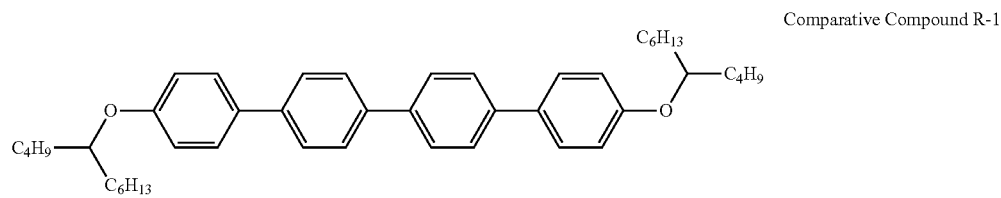

Comparative Compound R-1

TABLE 1

Two-Photon Absorption Cross-Sectional Area

| Compound | Two-Photon Absorption Cross-Sectional Area (GM) | Two-Photon Absorption Measurement Wavelength (nm) | Remarks |
| --- | --- | --- | --- |
| D-11 | 80 | 516 | Invention |
| D-405 | 770 | 405 | Invention |
| D-41 | 300 | 405 | Invention |
| D-42 | 560 | 405 | Invention |
| R-1 | 15 | Vicinity of 525 | Value in document, comparative example |
| R-2 | 200 | 550 | Comparative Example |

1 GM = 1 × 10$^{-50}$ cm$^4$ s molecule$^{-1}$ photon$^{-1}$

<Evaluation of Solubility of Two-Photon Absorption Compound>

The solubility of the compounds of the invention D-11, D-41 and D-405 and comparative compound R-2 in dichloromethane and 2-butanone is evaluated. The solubility of the compounds of the invention D-11, D-41 and D-405 are shown in Table 2 below as a relative value to solubility of comparative compound R-2.

TABLE 2

Evaluation of Solubility of Two-Photon Absorption Compound

| Compound | Solubility (dichloromethane) | Solubility (2-butanone) | Remarks |
| --- | --- | --- | --- |
| D-11 | 149 | 374 | Invention |
| D-41 | 93 | 117 | Invention |
| D-405 | 9 | 2.2 | Invention |
| R-2 | 1 | 1 | Comparative Example |

(At room temperature)

As shown in Table 2, the compounds in the invention have high solubility as compared with the comparative compound.

<Preparation of Two-Photon Absorption Recording Material (A)>
(Preparation of Two-Photon Absorption Recording Material 1)

Two-photon absorption recording material 1 is prepared with the following composition.

| | |
|---|---|
| Two-photon absorption compound: D-11 | 14 parts by mass |
| Dye precursor: DP-1 | 5.0 parts by mass |
| Acid generator: PAG-1 | 5.0 parts by mass |
| Binder: polyvinyl acetate (Mw: 113,000) | 100 parts by mass |
| Coating solvent: dichloromethane | 2,800 parts by mass |

(Preparation of Two-Photon Absorption Recording Material 2)

Two-photon absorption recording material 2 is prepared with the following composition.

| | |
|---|---|
| Two-photon absorption compound: D-41 | 17 parts by mass |
| Dye precursor: DP-1 | 5.0 parts by mass |
| Acid generator: PAG-1 | 5.0 parts by mass |
| Binder: polyvinyl acetate (Mw: 113,000) | 100 parts by mass |
| Coating solvent: dichloromethane | 2,800 parts by mass |

(Preparation of Comparative Two-Photon Absorption Recording Material 1 (Comparative Material 1))

Comparative material 1 is prepared with the following composition.

| | |
|---|---|
| Two-photon absorption compound: R-2 | 1.5 parts by mass |
| Dye precursor: DP-1 | 5.0 parts by mass |
| Acid generator: PAG-1 | 5.0 parts by mass |
| Binder: polyvinyl acetate (Mw: 113,000) | 100 parts by mass |
| Coating solvent: dichloromethane | 2,800 parts by mass |

Since comparative compound R-2 is small in solubility, the addition amount cannot be increased more than the above composition.

(Preparation of Two-Photon Absorption Recording Material 3)

Two-photon absorption recording material 3 is prepared with the following composition.

| | |
|---|---|
| Two-photon absorption compound: D-11 | 14 parts by mass |
| Monomer: M-1 | 92 parts by mass |
| Polymerization initiator: I-1 | 2.0 parts by mass |
| Binder: cellulose acetate butyrate (Mw: 40,000) | 100 parts by mass |
| Coating solvent: dichloromethane | 2,900 parts by mass |

(Preparation of Two-Photon Absorption Recording Material 4)

Two-photon absorption recording material 4 is prepared with the following composition.

| | |
|---|---|
| Two-photon absorption compound: D-41 | 17 parts by mass |
| Monomer: M-1 | 92 parts by mass |
| Polymerization initiator: I-1 | 2.0 parts by mass |
| Binder: cellulose acetate butyrate (Mw: 40,000) | 100 parts by mass |
| Coating solvent: dichloromethane | 2,900 parts by mass |

(Preparation of Comparative Two-Photon Absorption Recording Material 2 (Comparative Material 2))

Comparative material 2 is prepared with the following composition.

| | |
|---|---|
| Two-photon absorption compound: R-2 | 1.5 parts by mass |
| Monomer: M-1 | 92 parts by mass |
| Polymerization initiator: I-1 | 2.0 parts by mass |
| Binder: cellulose acetate butyrate (Mw: 40,000) | 100 parts by mass |
| Coating solvent: dichloromethane | 2,900 parts by mass |

Since comparative compound R-2 is small in solubility, the addition amount cannot be increased more than the above composition.

(Preparation of Two-Photon Absorption Recording Material 5)

Two-photon absorption recording material 5 is prepared with the following composition.

| | |
|---|---|
| Two-photon absorption compound: D-11 | 72 parts by mass |
| Dye precursor: DP-1 | 2.1 parts by mass |
| Binder: polyvinyl acetate (Mw: 113,000) | 500 parts by mass |
| Coating solvent: dichloromethane | 14,400 parts by mass |

(Preparation of Two-Photon Absorption Recording Material 6)

Two-photon absorption recording material 6 is prepared with the following composition.

| | |
|---|---|
| Two-photon absorption compound: D-41 | 87 parts by mass |
| Dye precursor: DP-1 | 2.1 parts by mass |
| Binder: polyvinyl acetate (Mw: 113,000) | 500 parts by mass |
| Coating solvent: dichloromethane | 14,400 parts by mass |

(Preparation of Comparative Two-Photon Absorption Recording Material 3 (Comparative Material 3))

Comparative material 3 is prepared with the following composition.

| | |
|---|---|
| Two-photon absorption compound: R-2 | 7.5 parts by mass |
| Dye precursor: DP-1 | 2.1 parts by mass |
| Binder: polyvinyl acetate (Mw: 113,000) | 500 parts by mass |
| Coating solvent: dichloromethane | 14,400 parts by mass |

Since comparative compound R-2 is small in solubility, the addition amount cannot be increased more than the above composition.

Used dye precursor DP-1, acid generator PAG-1, monomer M-1 and polymerization initiator I-1 are shown below.

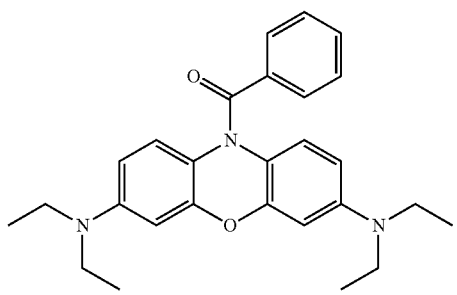

Dye Precursor DP-1

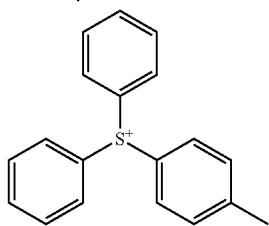

CF$_3$SO$_3^-$

Acid Generator PAG-1

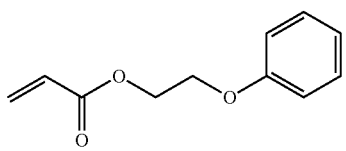

Monomer M-1

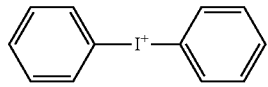

Polymerization Initiator I-1

<Manufacture of Two-Photon Absorption Recording Medium>

Each two-photon absorption recording medium in the invention is manufactured as a thin film having a dry film thickness of 1 µm by coating each of two-photon absorption recording materials 1 to 6 on a slide glass by spin coating. The comparative medium is also manufactured by spin coating. The recording medium obtained from two-photon absorption recording material 1 is taken as two-photon absorption recording medium 1. Other recording media are also the same.

<Evaluation of Two-Photon Recording Performance>

Second harmonic 522 nm of femto-second laser of 1,045 nm (pulse duration: 200 fs, repetition: 2.85 GHz, peak power: 1 kW) is used in two-photon recording. As for readout of recorded signals, fluorescence signals generated by irradiation of He—Ne laser ray of 632 nm is read out in the case of materials modulating fluorescence (two-photon absorption recording materials 5 and 6, and comparative material 3), and reflected light signals by irradiation of semiconductor laser ray of 405 nm is read out in the case of materials modulating a refractive index (two-photon absorption recording materials 1 to 4 and comparative materials 1 and 2). Whether it is two-photon recording or not is evaluated such that dependency on recording light intensity of readout signals is measured, and when signal intensity is proportioned to the square of recording light intensity, it is evaluated that recording by two-photon absorption has been done (evaluation of quadratic dependency). The results obtained are shown in Table 3 below.

TABLE 3

Results of Evaluation of Two-Photon Recording Performance

| Recording Medium | Dependency on Recording Light Intensity of Readout Signal | Presence or Absence of Quadratic Dependency | Judgment | Signal Intensity |
|---|---|---|---|---|
| Two-photon Recording medium 1 | Quadratic | Present | Two-photon recording | 1 |
| Two-photon Recording medium 2 | Quadratic | Present | Two-photon recording | 1.3 |
| Comparative Medium 1 | Quadratic | Present | Two-photon recording | 0.2 |
| Two-photon Recording medium 3 | Quadratic | Present | Two-photon recording | 1 |
| Two-photon Recording medium 4 | Quadratic | Present | Two-photon recording | 1.3 |
| Comparative Medium 2 | Quadratic | Present | Two-photon recording | 0.1 |
| Two-photon Recording medium 5 | Quadratic | Present | Two-photon recording | 1 |
| Two-photon Recording medium 6 | Quadratic | Present | Two-photon recording | 1.5 |
| Comparative Medium 3 | Quadratic | Present | Two-photon recording | 0.4 |

Each of two-photon absorption recording materials 1 to 6 and comparative materials 1 to 3 can effect two-photon absorption, but two-photon absorption dye R-2 used in comparative materials 1 to 3 is small in solubility and the addition amount cannot be increased, and so both recording sensitivity and signal intensity are small.

<Preparation of Two-Photon Absorption Recording Material (B)>

(Preparation of Two-Photon Absorption Recording Material 11)

Two-photon absorption recording material 11 is prepared with the following composition.

| | |
|---|---|
| Two-photon absorption compound: D-11 | 215 parts by mass |
| Polymer binder: polyvinyl acetate (Mw: 111,300) | 500 parts by mass |
| Coating solvent: dichloromethane | 14,400 parts by mass |

(Preparation of Two-Photon Absorption Recording Material 12)

| | |
|---|---|
| Two-photon absorption compound: D-405 | 85 parts by mass |
| Polymer binder: polyvinyl acetate (Mw: 111,300) | 500 parts by mass |
| Coating solvent: dichloromethane | 14,400 parts by mass |

(Preparation of Comparative Two-Photon Absorption Recording Material 11 (Comparative Material 11))

| Two-photon absorption compound: R-2 | 8 parts by mass |
|---|---|
| Polymer binder: polyvinyl acetate (Mw: 111,300) | 500 parts by mass |
| Coating solvent: dichloromethane | 14,400 parts by mass |

<Preparation of Two-Photon Absorption Recording Medium>

Each of two-photon absorption recording media 7 and 8 in the invention is manufactured as a thin film having a dry film thickness of 1 μm by coating each of two-photon absorption recording materials 11 and 12 respectively on a slide glass by spin coating. The refractive index of the glass substrate is 1.53.

Comparative medium 4 is manufactured by using comparative two-photon recording material 11 in the similar manner to the manufacture of two-photon absorption recording media 7 and 8.

<Test and Evaluation Methods of Two-Photon Recording and Readout>

A recording layer is irradiated with a recording light (pulse laser: wavelength of 522 nm, repeating frequency: 3 GHz, pulse duration: 500 fsec, average power Pa: 5 to 50 mW, peak power Pp: 3 to 33 W) by a peak power of 10 W.

The focal position of recording light is moved every 0.4 μm in the range of 4 μm in optical axis direction to the recording layer (that is, positions of 11 points in the depth direction), and recording of four points (i.e., recording at 44 spots in total) is tested at each depth position (focal position).

As recording condition, recording time is adjusted between 5 μs and 5 ms, and recording time [μs] capable of recording 12 recording marks (3 spots at contiguous focal positions and 4 spots at every focal position) at a time is obtained as data.

<Results of Evaluation of Two-Photon Recording Sensitivity>

The results of evaluation of two-photon recording sensitivity are shown in Table 4 below.

TABLE 4

Results of Evaluation of Two-Photon Recording Sensitivity

| Recording Medium | Time Required for Recording (μsec) |
|---|---|
| Two-photon absorption recording medium 7 | 30 |
| Two-photon absorption recording medium 8 | 40 |
| Comparative medium 4 | Recording is impossible. |

INDUSTRIAL APPLICABILITY

According to the constitution of the two-photon absorption recording material of the invention, it is possible to perform non-resonant two-photon absorption recording using a recording light in a wavelength region shorter than 700 nm in high sensitivity and obtain sufficient recording and readout properties.

In addition, the two-photon absorption compound in the invention shows non-resonant two-photon absorption properties by the recording light in a wavelength region shorter than 700 nm and high two-photon absorption cross sectional area can be obtained. Further, the two-photon absorption compound in the invention has high solubility and can be contained in the two-photon absorption recording material in high concentration, and so high recording sensitivity can be obtained by the recording material.

The entire disclosure of Japanese Patent Application No. 2010-33910 filed on Feb. 18, 2010 and Japanese Patent Application No 2010-220085 filed on Sep. 29, 2010, from which the benefit of foreign priority has been claimed in the present application, is incorporated herein by reference, as if fully set forth.

The invention claimed is:

1. A non-resonant two-photon absorption recording material comprising:
   (a) a non-resonant two-photon absorption compound, and
   (b) a recording component in which at least either refractive index or fluorescence intensity changes,
   wherein the non-resonant two-photon absorption compound (a) is a compound having the structure represented by the following formula (1):

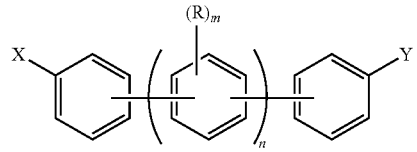

Formula (1)

wherein each of X and Y represents a substituent having a Hammett's sigma para-value (σp value) of 0 or more, which may be the same with or different from each other; n represents an integer of 1 to 4; R represents a substituent, and a plurality of R's may be the same with or different from every other R; and m represents an integer of 0 to 4, provided that when n is 1, m is 1 or more, and when n is 2 or more, at least any of n-groups of phenylene groups is m≧1.

2. The non-resonant two-photon absorption recording material according to claim 1, wherein the non-resonant two-photon absorption compound having the structure represented by formula (1) is a compound having the structure represented by the following formula (2):

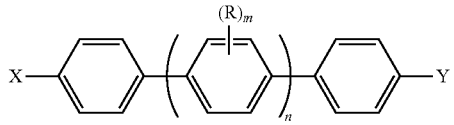

Formula (2)

wherein each of X and Y represents a substituent having a Hammett's sigma para-value (σp value) of 0 or more, which may be the same with or different from each other; n represents an integer of 1 to 4; R represents a substituent, and a plurality of R's may be the same with or different from every other R; and m represents an integer of 0 to 4, provided that when n is 1, m is 1 or more, and when n is 2 or more, at least any of n-groups of phenylene groups is m≧1.

3. The non-resonant two-photon absorption recording material according to according to claim 1, wherein the non-resonant two-photon absorption compound having the structure represented by formula (1) or (2) is a compound having the structure represented by the following formula (3):

Formula (3)

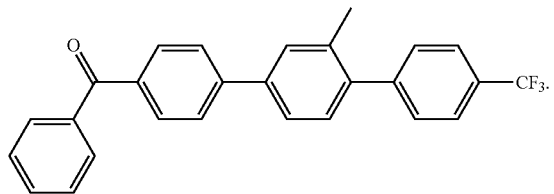

4. The non-resonant two-photon absorption recording material according to according to claim 1, wherein the non-resonant two-photon absorption compound having the structure represented by formula (1) or (2) is a compound having the structure represented by the following formula (4):

Formula (4)

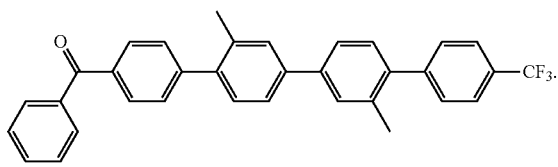

5. The non-resonant two-photon absorption recording material according to according to claim 1, wherein the non-resonant two-photon absorption compound having the structure represented by formula (1) or (2) is a compound having the structure represented by the following formula (5):

Formula (5)

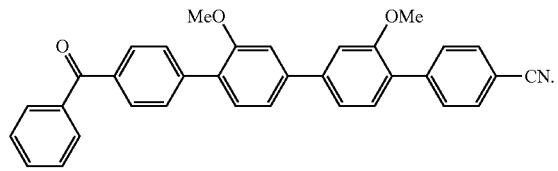

6. The non-resonant two-photon absorption recording material according to claim 1, wherein the component (b) is a material capable of modulating a refractive index by polymerization of a dye having a polymerizable group.

7. A non-resonant two-photon absorption recording material comprising:
(a) a non-resonant two-photon absorption compound, and
(b') a polymer binder,
wherein the non-resonant two-photon absorption compound (a) is a compound having the structure represented by the following formula (1):

Formula (1)

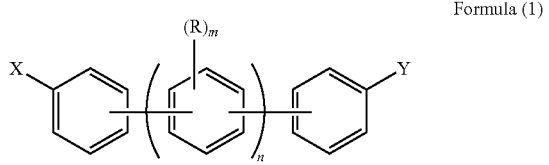

wherein each of X and Y represents a substituent having a Hammett's sigma para-value (σp value) of 0 or more, which may be the same with or different from each other; n represents an integer of 1 to 4; R represents a substituent, and a plurality of R's may be the same with or different from every other R; and m represents an integer of 0 to 4, provided that when n is 1, m is 1 or more, and when n is 2 or more, at least any of n-groups of phenylene groups is m≧1.

8. The non-resonant two-photon absorption recording material according to claim 7, wherein the non-resonant two-photon absorption compound having the structure represented by formula (1) is a compound having the structure represented by the following formula (2):

Formula (2)

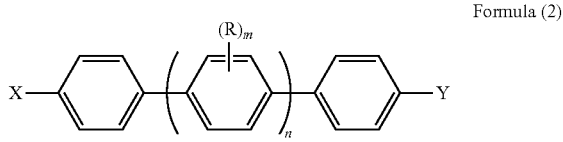

wherein each of X and Y represents a substituent having a Hammett's sigma para-value (σp value) of 0 or more, which may be the same with or different from each other; n represents an integer of 1 to 4; R represents a substituent, and a plurality of R's may be the same with or different from every other R; and m represents an integer of 0 to 4, provided that when n is 1, m is 1 or more, and when n is 2 or more, at least any of n-groups of phenylene groups is m≧1.

9. The non-resonant two-photon absorption recording material according to according to claim 7, wherein the non-resonant two-photon absorption compound having the structure represented by formula (1) or (2) is a compound having the structure represented by the following formula (3):

Formula (3)

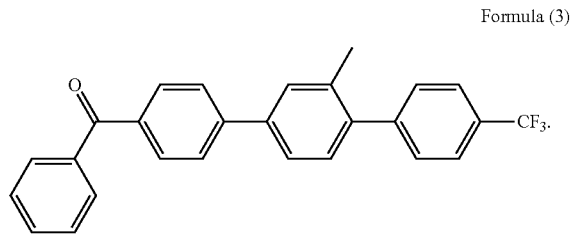 [SMILES: Cc1cc(-c2ccc(C(=O)c3ccccc3)cc2)ccc1-c1ccc(C(F)(F)F)cc1]

10. The non-resonant two-photon absorption recording material according to according to claim 7, wherein the non-resonant two-photon absorption compound having the structure represented by formula (1) or (2) is a compound having the structure represented by the following formula (4):

Formula (4)

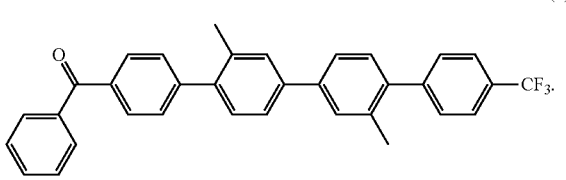

11. The non-resonant two-photon absorption recording material according to according to claim 7, wherein the non-resonant two-photon absorption compound having the structure represented by formula (1) or (2) is a compound having the structure represented by the following formula (5):
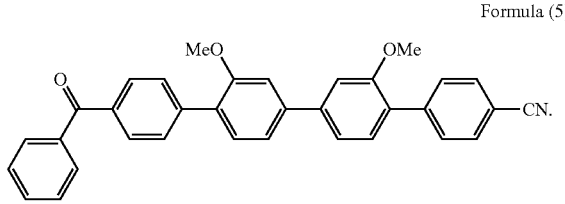
Formula (5)
12. A compound having the structure represented by the following formula (3):
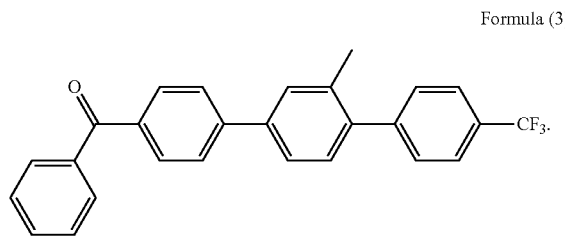
Formula (3)
13. A compound having the structure represented by the following formula (4):
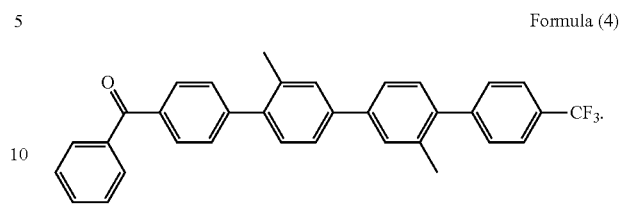
Formula (4)
14. A compound having the structure represented by the following formula (5):
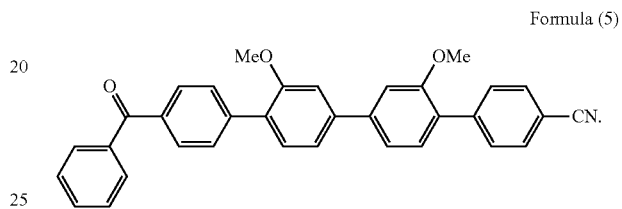
Formula (5)
\* \* \* \* \*